(12) United States Patent
Maples et al.

(10) Patent No.: US 6,955,872 B2
(45) Date of Patent: Oct. 18, 2005

(54) DYE COMPOSITIONS WHICH PROVIDE ENHANCED DIFFERENTIAL FLUORESCENCE AND LIGHT SCATTER CHARACTERISTICS

(75) Inventors: John A. Maples, Miami, FL (US); Lidice L. Lopez, Miami, FL (US); Nancy Torke, Miami, FL (US)

(73) Assignee: Coulter International Corp., Miami, FL (US)

( * ) Notice: Subject to any disclaimer, the term of this patent is extended or adjusted under 35 U.S.C. 154(b) by 206 days.

(21) Appl. No.: 10/392,518

(22) Filed: Mar. 20, 2003

(65) Prior Publication Data

US 2004/0185447 A1 Sep. 23, 2004

(51) Int. Cl.[7] .................................................. C12Q 1/68
(52) U.S. Cl. .............................................. 435/4; 435/6
(58) Field of Search ........................ 435/6, 91.1, 92.2; 436/8, 10, 17, 63, 164, 172

(56) References Cited

U.S. PATENT DOCUMENTS

| | | | |
|---|---|---|---|
| 3,962,125 A | | 6/1976 | Armstrong |
| 4,325,706 A | | 4/1982 | Gershman et al. |
| 4,745,285 A | * | 5/1988 | Recktenwald et al. ... 250/458.1 |
| 4,933,293 A | | 6/1990 | Kuroda et al. |
| 4,957,870 A | | 9/1990 | Lee et al. |
| 4,971,917 A | | 11/1990 | Kuroda |
| 5,534,416 A | * | 7/1996 | Millard et al. ................. 436/34 |
| 5,691,204 A | | 11/1997 | Kim et al. |
| 6,060,322 A | | 5/2000 | Horton et al. |
| 6,197,593 B1 | * | 3/2001 | Deka et al. .................... 436/63 |
| 6,271,035 B1 | * | 8/2001 | Deka et al. .................... 436/10 |

OTHER PUBLICATIONS

Spanish Multicentric Study Group for Hematopoietic Recovery, "Flow cytometric reticulocyte quantification in the evaluation of hematologic recovery", Eur J Haematol 1994: 53: 293–297.

Barkan, D., et al., "Optimisation of flow cytometric measurement of parasitaemia in plasmodium–infected mice", Intl J for Parasitology 30 (2000) 649–653.

Darzynkiewicz, Z., et al., "Application of Pyronin Y(G) in Cytochemistry of Nucleic Acids", Cytometry 8: 138–145 (1987).

Davis, B.H., et al., "Flow Cytometric Reticulocyte Analysis", Am J Clin Pathol, 102:468–477 (1994).

Makler, M.T., et al., "Thiazole Orange: A New Dye for Plasmodium Species Analysis", Cytometry 8:568–570 (1987).

Peebles, D.A., et al., "Analysis of Manual Reticulocyte Counting", Am J Clin Pathol, 76:713–717 (1981).

Shapiro, Howard M., "Flow Cytometric Estimation of DNA and RNA content in Intact Cells Stained with Hoechst 33342 and Pyronin Y", Cytometry, 2(3):143–150 (1981).

Van Vianen, P.H., "Flow Cytometric Screening of Blood Samples for Malaria Parasites", Cytometry, 14:276–280 (1993).

* cited by examiner

Primary Examiner—Kenneth R. Horlick
Assistant Examiner—Heather G. Calamita
(74) Attorney, Agent, or Firm—Howson and Howson; Mitchell E. Alter

(57) ABSTRACT

A composition for enhancing differential staining of RNA, DNA and granules in a sample comprising cells contains a first fluorescent dye that can bind specific binding sites and non-specific binding sites in the sample. This first dye emits fluorescence at a first wavelength. The composition contains at least an additional component, which is a second non-intercalating dye in the composition that competes with said first dye for binding to the nonspecific binding sites, or a permeabilizing agent to enhance permeabilization of the dyes into the cells, or both. The molar ratio of the second dye and the first dye is at least about 20:1.

40 Claims, 6 Drawing Sheets

Sphering Reagent

Thiazole Orange + Sphering Reagent

Thiazole Orange + Sphering Reagent + Hoechst dye

Sphering Reagent

Thiazole Orange + Sphering Reagent

Thiazole Orange + Sphering Reagent + Hoechst dye

DYE COMPOSITIONS WHICH PROVIDE ENHANCED DIFFERENTIAL FLUORESCENCE AND LIGHT SCATTER CHARACTERISTICS

BACKGROUND OF THE INVENTION

Several characteristics permit the identification and discrimination of different cells obtained from a variety of sources by cell type for diagnostic and research purposes. Such characteristics include the size of the cells, the forward light scattering properties of the cells, the 90° light scattering of the cells, the number and type of acidophilic or basophilic granules contained in the cells, the amount of RNA contained in the cells, the condensation of the nuclear chromatin of the cells, the cytoplasm to nuclear ratio of the cells, the physical appearance of nucleoli of the cells, and the number of mitochondria contained in the cells, among others.

The classical use of fluorescent dyes to discriminate cells, especially cells found in whole blood, is usually associated with staining the cell's nucleus or DNA. Many cells have the same amount of DNA, and if such cells are stained using a fluorescent dye, the DNA in each cell is similarly stained. Therefore, discriminating between different blood cells, for example, including lymphocytes, monocytes, neutrophils, eosinophils, basophils, and nucleated red blood cells, among others, is difficult, if not impossible.

There are several fluorescent dyes that have been used to analyze cells and include metachromatic dyes. Metachromatic dyes have excitation and emission wavelengths that shift depending on the manner in which the compound or cell that binds the dye. For example, a metachromatic dye can emit at one wavelength when it binds RNA and at another wavelength when it binds DNA. One common metachromatic dye is Acridine Orange dye (AO), which, when bound to double stranded DNA, has an absorption maximum of 502 nm and an emission maximum of 520 to 524 nm. When AO is bound to single stranded DNA or RNA, it has an absorption maximum of 526 to 558 nm and an emission maximum of 630 to 644 nm. AO also can accumulate in the lysosome granules where it has an emission wavelength of about 630 nm. AO is also known to accumulate in the alpha granules of platelets and the granules of mast cells.

The separation and identification of wavelength differences in cellular identification using metachromatic dyes has been observed (Melamed et al. 1972 *Amer. J. Clin. Path.*, 57:95–102). Specifically, in nucleated cells, the ability to resolve metachromatic staining of nucleated cells at the red wavelengths decreased or was lost, i.e., the 520 to 524 nm emission maximum overlapped into the weaker red fluorescence of the RNA or granules. These authors hypothesized that the same was due to the large amount of DNA staining, the intense fluorescence obtained therefrom, and broad emission spectrum obtained. For reticulocytes, weak RNA staining was superimposed on the nonspecific interaction and fluorescence of the dye into cellular material.

The Acridine Orange metachromatic dye was also used to detect reticulocytes using the red fluorescence and forward scatter to discriminate a cell from noise and to distinguish platelets from reticulocytes and red blood cells. See U.S. Pat. No. 4,325,706.

The difficulties in using dyes including AO are known by those of skill in the art. See, "Flow Cytometry and Cell Sorting" *Acridine Orange: A Versatile Probe of Nucleic Acids and Other Cell Constituents;* $2^{nd}$ Ed., Wiley-Liss, Inc.: pages 291–314 (1990). Specifically, it is known that metachromatic dyes such as AO, do not follow the simple laws of mass action in their staining. The dye often causes a phase transition (condensation or precipitation) in binding to the target material. Further, such dyes require precise control of dye concentration, free dye concentration, cell concentration, pH, time, and temperature to obtain reproducibility. Precise control is difficult or impossible to obtain in routine applications.

Equilibrium staining methods employing AO have been used for DNA/RNA content measurement, but are noted to be difficult to apply to intact cells and impractical for use with fluorescent antibodies or ligands for demonstration of cell surface structures. Therefore, others have turned to combinations of other dyes, such as Hoechst 33342 and pyronin Y (i.e., a xanthine analog of AO) at a 2:1 to 1:1 ratio, and Hoechst 33342 and AO at a 5:1 ratio, to stain intact cells for DNA/RNA content with a dual source flow cytometer (H. M. Shapiro, 1981 *Cytometry,* 2(3):143–150). However, unstable results were reportedly obtained with the AO combination. These authors reported an accurate estimate of DNA content and biased estimate of RNA content with the Hoechst 33342/pyronin Y combination.

There remains a need in the art for dyes and dye combinations suitable for differential staining fluorescent dyes and/or combinations thereof for effective cellular identification.

SUMMARY OF THE INVENTION

In one aspect, the invention provides a composition for enhancing differential staining of RNA, DNA and granules in a sample containing cells. The composition includes a first fluorescent dye that binds both specific binding sites and non-specific binding sites in the sample and that emits fluorescence at a first wavelength. In one embodiment, the composition further includes a second non-intercalating dye that competes with the first dye for binding to the nonspecific binding sites. An additional component, a permeabilizing agent may be included in the composition to enhance permabilization of the first dye into cells in the samples. In some embodiments, the molar ratio of the second dye and the first dye is at least about 20:1. In another embodiment, the composition contains a first dye, a second dye and a permeabilizing reagent as described herein.

In another aspect, the invention provides a method for enhancing differential staining of RNA, DNA and granules in a sample containing cells. This method involves contacting said sample with a dye composition as described herein, and analyzing the sample to detect differential expression of nucleic acids and granules in the sample.

Other aspects and advantages of the present invention are described further in the following detailed description of the preferred embodiments thereof.

1A over time. The point of discrimination between bright and dim staining varies over the analysis time.

Figure 1A:
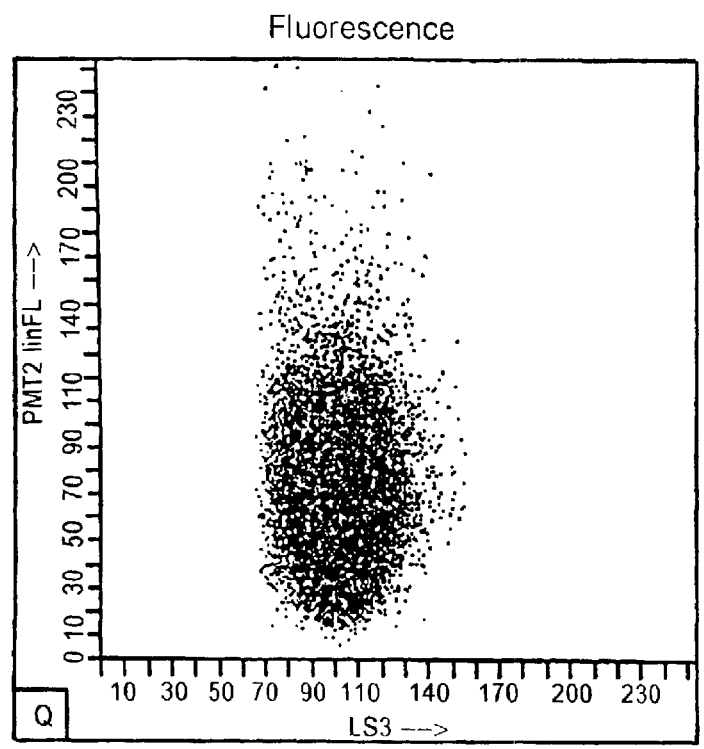
FIG. 1A is a cytogram plotting fluorescence vs. light scatter, showing the fluorescence signals from nucleic acids (e.g., RNA) in a sample of reticulocytes that was treated with AO dye and a permeabilizing agent without a second non-intercalating dye/blocking agent (see Example 3 below). The identification of reticulocytes is dependent upon the ability to determine where the negative ends and the positive starts, as can be seen by the difference between the brightly stained and dimly stained portions of the cytogram.
Figure 1B:
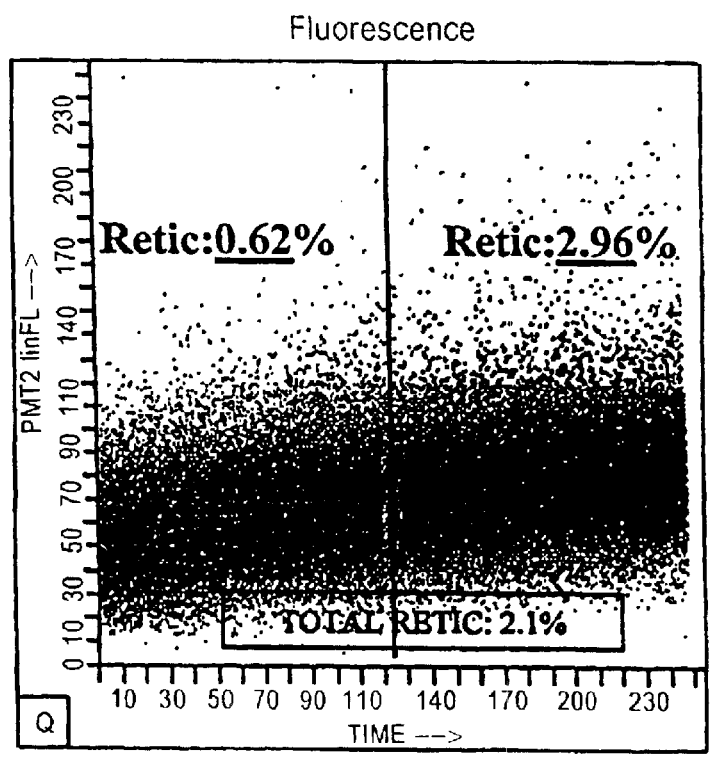
FIG. 1B is a cytogram showing the fluorescence signals from nucleic acids in the same sample as described in FIG.
Figure 1C:
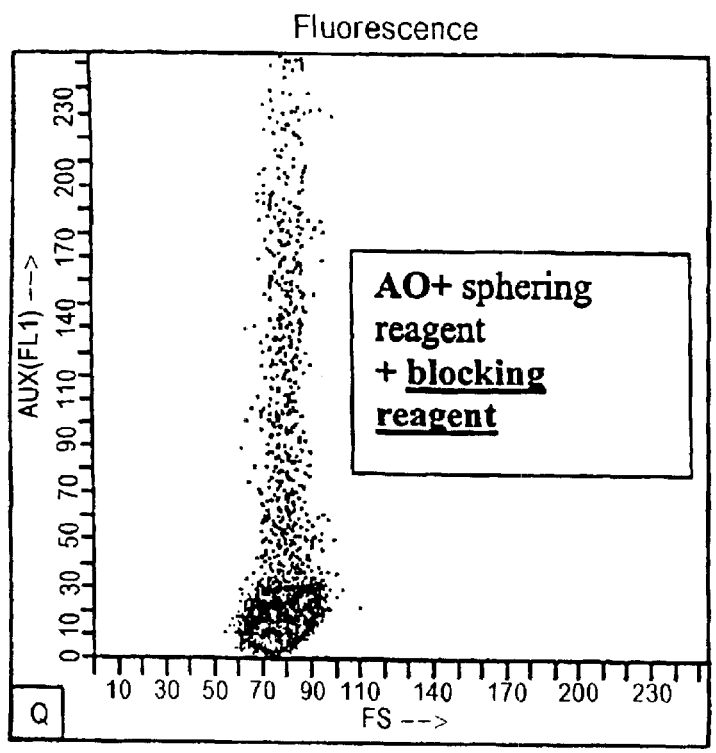

FIG. 1C is a cytogram showing the fluorescence signals from nucleic acids in a sample of reticulocytes that was treated with a composition of the invention containing the first dye AO, the second dye (blocking reagent) Hoechst 33258, with a permeabilizing agent (sphering agent). This figure, plotting fluorescence vs. forward scatter, demonstrates the total population of dim reticulocytes (close to the RBC negative population) and the bright reticulocytes. See Example 3 below. The use of the present invention reduces kinetics, improves incubation time and permits a more accurate analysis of the sample.

Figure 1D:
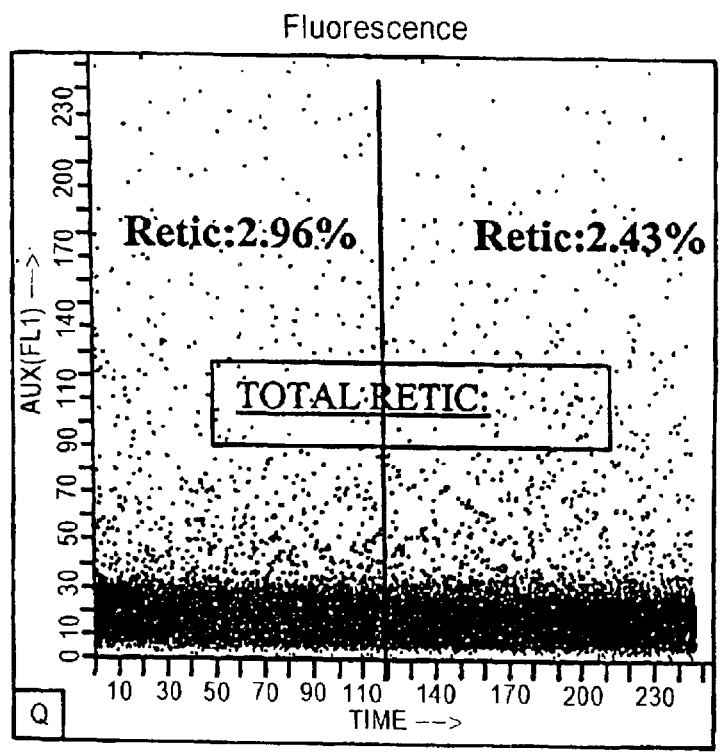

FIG. 1D is a cytogram showing the fluorescence signals from nucleic acids in a sample of reticulocytes as in FIG. 1C over time. This figure demonstrates the ability of the discrimination between cell types to stay constant.

Figure 2A:
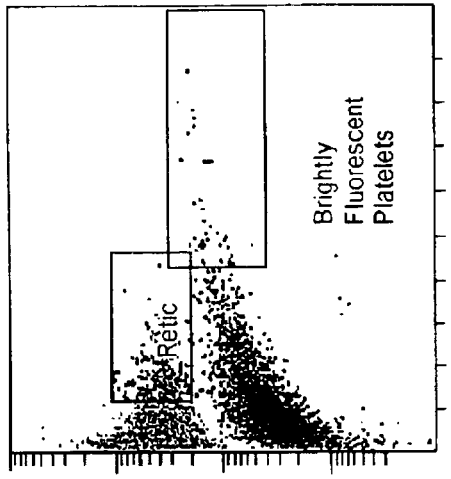

FIG. 2A is a cytogram showing differential discrimination using low angle light scatter (forward scatter) of platelets and RBCs in a sample treated with a composition of this invention, i.e., a first dye AO, the second dye (blocking reagent) Hoechst 33258, and a permeabilizing agent. No platelet antibody was used in this sample.

Figure 2B:
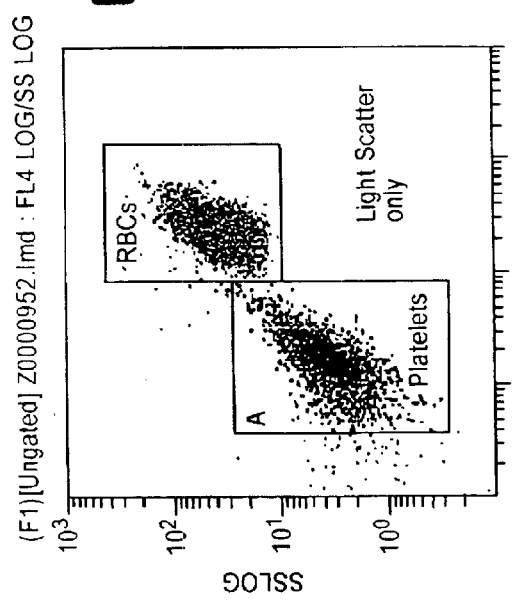

FIG. 2B is a cytogram showing brightly fluorescent platelets stained as in FIG. 2A and measured for fluorescence at a wavelength of between 675–725 nm. The invention allows the nucleic acids to be distinguishable.

Figure 2C:
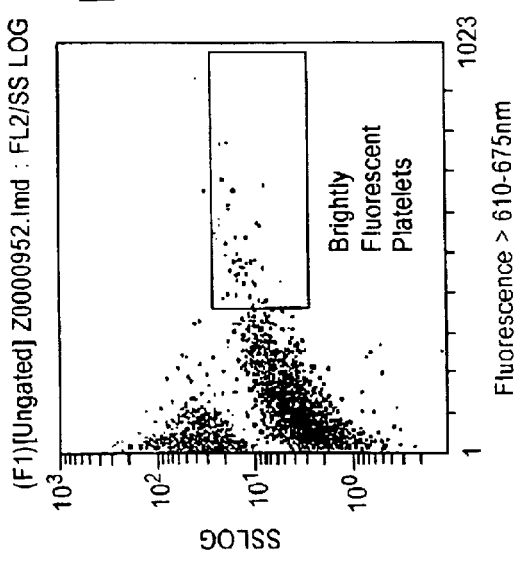

FIG. 2C is a cytogram showing brightly fluorescent platelets stained as in FIG. 2B and measured for fluorescence at a wavelength of between 610 and 675 nm.

FIGS. 3A–3G are cytograms comparing ROG cells treated with sphering reagent (permeabilizing agent) only, a composition containing a first dye and a permeabilizing agent, or a composition containing a first dye, a second dye and a permeabilizing agent. The cytograms show increasing discrimination of the various nucleic acid components of the ROG cells, in these instances particularly of the large lower mass of platelets. Similar results can be obtained when the samples are gated on platelets (not shown).

Figure 3A:
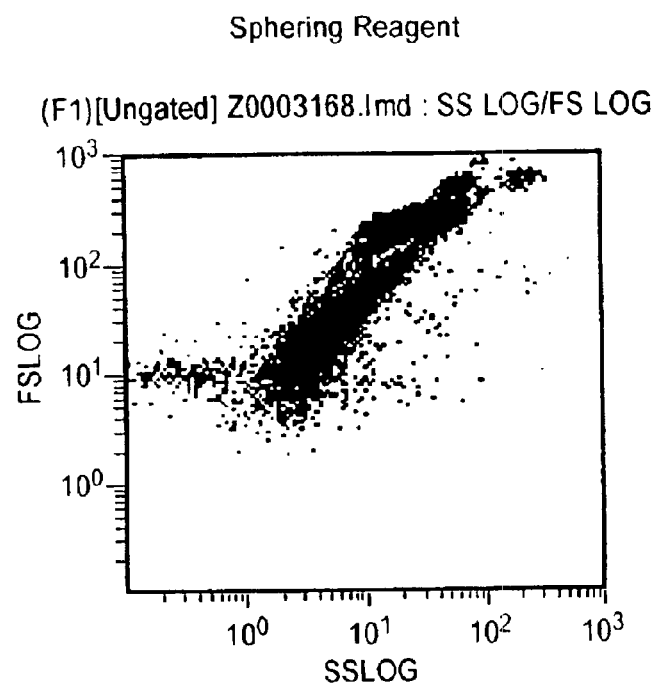

FIG. 3A is a cytogram (light scatter vs. light scatter) showing the distribution of platelets, RBC, RBC doublets and WBC in ROG cells treated with a permeabilizing agent (sphering reagent).

Figure 3B:
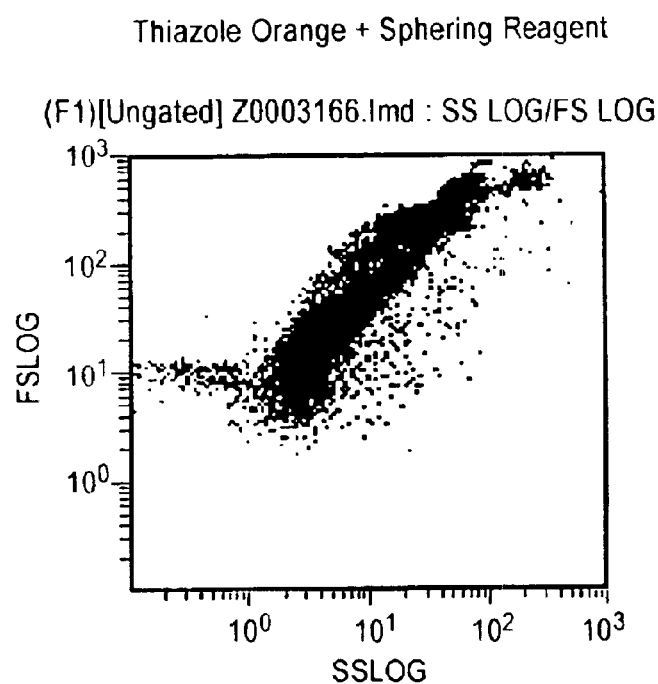

FIG. 3B is a cytogram (light scatter vs. light scatter) showing the distribution of platelets, RBC, RBC doublets and WBC in of ROG cells treated with a first dye (e.g., Thiazole Orange) and a permeabilizing agent.

Figure 3C:
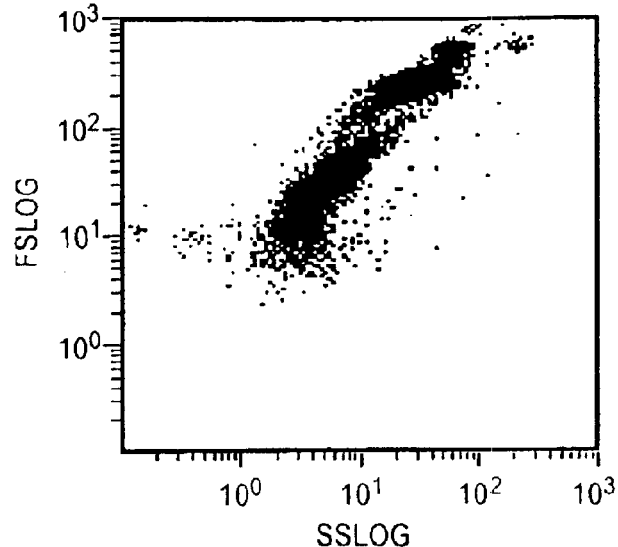

FIG. 3C is a cytogram (light scatter vs. light scatter) showing the distribution of platelets, RBC, RBC doublets and WBC in of ROG cells treated with a first dye (e.g., Thiazole Orange), a second dye (Hoechst dye) and a permeabilizing agent.

Figure 3D:
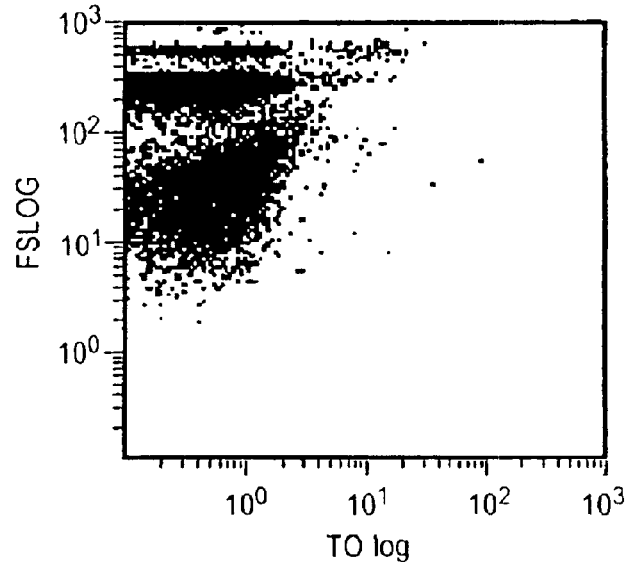

FIG. 3D is a cytogram (light scatter vs. fluorescence) showing the distribution of platelets, RBC, RBC doublets and WBC in ROG cells treated with a permeabilizing agent (sphering reagent).

Figure 3E:
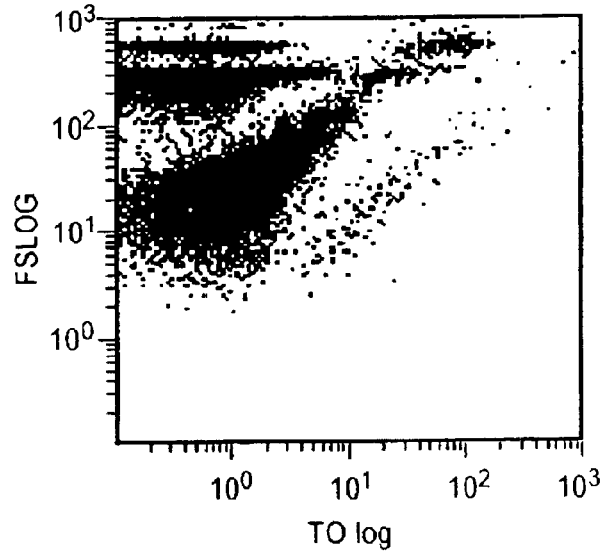

FIG. 3E is a cytogram (light scatter vs. fluorescence) showing the distribution of platelets, RBC, RBC doublets and WBC in ROG cells treated with a first dye (e.g., Thiazole Orange) and a permeabilizing agent.

Figure 3F:
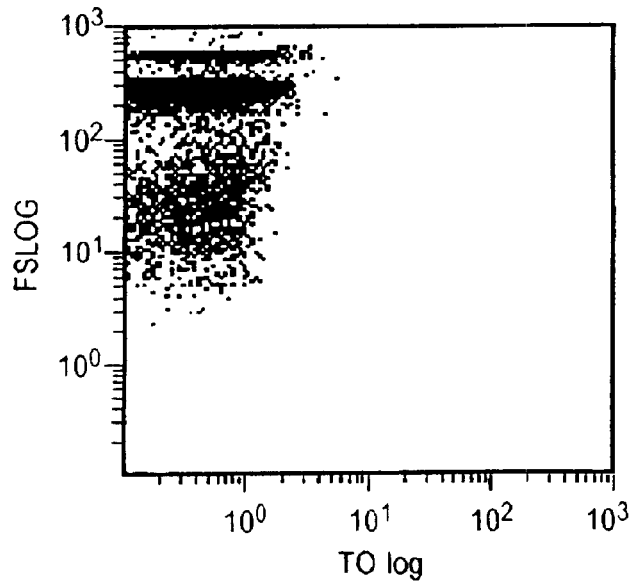

FIG. 3F is a cytogram (light scatter vs. fluorescence) showing the distribution of platelets, RBC, RBC doublets and WBC in ROG cells treated with a first dye (e.g., Thiazole Orange), a second dye (Hoechst dye) and a permeabilizing agent.

DETAILED DESCRIPTION OF THE INVENTION

The present invention provides dye compositions and methods that enhance the differential staining of nucleic acids and granules in a cell-containing sample. These compositions and methods are preferably employed in the discrimination of blood cells using flow cytometry or hematology equipment known in the art. These compositions and methods of the present invention permit the analysis and discrimination between cells of a sample and provide an advantage over the dyes and methods of use in the art in that the invention reduces or eliminates non-specific interactions of fluorescent dyes. The invention permits rapid uptake of the dye compositions into the cells. Other advantages of the present invention include, without limitation, improved light scatter and fluorescent resolution of immature and mature red blood cells which enhances the ability to formulate accurate algorithms for consistent automated analysis, an increase in the kinetics of the reaction between the nucleic acids and the dyes, a decrease in incubation times, and the elimination of added washing steps practiced in the prior art to remove non-specific binding.

I. The Compositions of the Invention

The compositions of the present invention contain a first fluorescent dye (primary dye) that can bind specific binding sites and non-specific binding sites in the sample. The first dye emits fluorescence at a first given wavelength. This composition can contain other fluorescent dyes in addition to the primary dye that specifically or preferentially stain selected components of a cell including, without limitation, double stranded DNA, single-stranded DNA, single-stranded RNA, acidophilic granules, basophilic granules, red blood cell inclusions, and/or intracellular parasites, including, e.g., viruses, among others.

In one embodiment, a composition of this invention includes a second non-intercalating dye or blocking agent that competes with the first dye for binding to the nonspecific binding sites. The blocking agent minimizes or eliminates non-specific interaction of the primary dye. More particularly, the inventors have discovered that by using an excess of the blocking agent in the composition of at least a molar ratio of 20:1, the blocking agent competes with the primary dye or dyes for the weak binding sites. When provided at this excess, binding of the primary dyes to its high affinity binding sites in the cells in preference to the low binding affinity, non-specific binding sites, is increased. This increase in selectivity of binding of the primary dye thereby increases the discrimination between the cells bearing the specific binding sites vs. those cells that bear non-specific binding sites for the primary dye. In one embodiment, the ratio of blocking reagent to primary dye in the compositions and methods of this invention is at least 50:1. In another embodiment, the ratio of blocking reagent to primary dye in the compositions and methods of this invention is at least 100:1. In still another useful embodiment, the ratio of blocking reagent to primary dye in the compositions and methods of this invention is at least 150:1. In still another useful embodiment, the ratio of blocking reagent to primary dye in the compositions and methods of this invention is at least 300:1. In still another useful embodiment, the ratio of blocking reagent to primary dye in the compositions and methods of this invention is at least 500:1. All ratios are molar, unless otherwise indicated.

In another embodiments, the composition combines the first and second dyes with a permeabilizing agent. In some embodiments using cell permeant first dyes, a permeabilizing agent may be used even in the absence of the second dye to increase discrimination. In either embodiment, the permeabilizing agent, such as a sphering agent, enhances permabilization of the primary dye(s) and/or blocking reagent into the cells.

A. Primary Dye Components

According to the present invention, preferably, the primary dye(s) used in the invention is a fluorescent dye. In one embodiment, the fluorescent dye is essentially non-fluorescent in the unbound state, thereby providing minimal background fluorescence. The primary dye preferably emits fluorescence at a given wavelength upon binding to a specific or non-specific binding site or target on a cell. An optional additional or "second" primary dye(s) useful in this invention can be selected from among non-fluorescent dyes which are differentially distinguishable, preferably by calorimetric or visual means. The "second" primary dye can be chosen for its ability to improve cell type and component discrimination in a selected analysis. The primary dye used in the invention detects cells and/or selected cellular components with high specificity.

It is desirable that, when irradiated, the primary dye emits (i.e., fluoresces, or is excited) at a wavelength different from the wavelength of other dyes and blocking reagents selected for inclusion in the composition. Preferably, there is no overlap between the fluorescence of the primary dye with other dyes or blocking agents at the wavelength chosen for detection. Using methods and information available in the art, one of skill in the art would readily be able to determine which dye would fluoresce at wavelengths that would overlap. See, The Handbook of Fluorescent Probes and Research Products, $6^{th}$ Ed., R. P. Haugland, Molecular Probes, Eugene, Oreg. Such is the case even in compositions containing two or more primary dyes, each of which may or may not be fluorescent. In one embodiment which contains only one primary dye which is fluorescent, the primary dye fluoresces at wavelengths above 500 nanometers, and more preferably, above 520 to 630 nm. However, dyes that fluoresce at other suitable wavelengths may be readily selected. In compositions or methods employing more than one primary dye, the additional dyes fluoresce at wavelengths different from that of the first primary dye.

In one embodiment, the primary dye selected is a metachromatic dye. By the phrase "metachromatic dye" is meant to describe a fluorescent dye that contains two or more peaks in its emission spectrum when bound to a cell or cellular components. Typically, a metachromatic dye fluoresces at different wavelengths when bound to different types of cells, i.e., to RNA, DNA, or other cellular components. For example, one metachromatic dye used according to the present invention fluoresces at different wavelengths when bound to double-stranded DNA, single-stranded DNA, or single-stranded RNA.

A variety of metachromatic dyes are known in the art and include, without limitation, xanthene dyes, carbocyanine dyes, polymethine dyes including Astra Violet FR, thiofalvine T, psuedoisocyanine, oxacarbocyanine dyes, acridine dyes, azine dyes, diphenylmethane dyes, methine dyes, oxazine dyes, cyanine dyes, and styryl dyes, among others. See, for example, the metachromatic dyes noted in Urban et al., 2000 Acta. Histochem. 102:259–272. A preferred metachromatic dye for use in one embodiment of this invention is the Acridine Orange dye ("AO", Polysciences, Warrington, Pa.). Still other metachromatic dyes that are useful in the invention include the nonyl Acridine Orange dye (3,6-Bis-(dimethylamino)-10-nonylacridinium bromide, Molecular Probes, Eugene, Oreg.); the Acridine Red™ dye (also commercially available as Pyronin B, Sigma-Aldrich Corp., St. Louis, Mo.), the Toluidine Blue dye (2-amino-7-dimethylamino-3-methylphenothiazinium chloride, Sigma-Aldrich Corp., St. Louis, Mo.), hydrosystilbamidine (Molecular Probes, Eugene, Oreg.) and cyanine dyes including the SYTO™ dyes (Molecular Probes, Eugene, Oreg.), the TOTO™ dyes (Molecular Probes, Eugene, Oreg.), the YOYO™ dyes (Molecular Probes, Eugene, Oreg.), the BOBO™ dyes (Molecular Probes, Eugene, Oreg.), among others, and combinations thereof. More preferably, the metachromatic dye is the Acridine Orange dye.

In a further embodiment, the primary dye is a non-metachromatic dye. By the term "non-metachromatic dye" is meant to describe a fluorescent dye that provides a single wavelength of excitation and/or emission when irradiated at a predetermined wavelength. Such dyes are useful in methods for discriminating multiple cell types or in circumstances in which a second fluorescent dye or antibody is present that has a metachromatic wavelength that interferes with analysis of the sample. Such dyes are effective in staining cellular components of cells including acidophilic granules, basophilic granules, and cellular membranes of the cells. Such dyes are particularly useful as "second" primary dyes in the compositions for staining at least one member of acidophilic granules of cells, basophilic granules of cells and cellular membranes.

Examples of non-metachromatic dyes include, without limitation, the Neutral Red™ dye (3-amino-7-dimethylamino-2-methylphenazine hydrochloride, Sigma-Aldrich Corp., St. Louis, Mo.), the Basic Orange™ 21 dye (Sigma-Aldrich Corp., St. Louis, Mo.), the DiOC dye (1,1'-dimethyloxacarbocyanine, Molecular Probes, Eugene, Oreg.), the Pyronin™ Y dye (Polysciences, Inc., Warrington, Pa.), the Methylene Blue™ dye (3-bis-(dimethylamino)-phenothiazin-5-ium chloride, Molecular Probes, Eugene, Oreg.), the Auramine™ O dye (4,4'-(imidocarbonyl)-bis-(N, N,-dimethylaniline) monohydrochloride, Sigma-Aldrich Corp., St. Louis, Mo.), the LDS™ 751 dye (quinolinium, 6-(dimethylamino)-2-[4-[4-(dimethylamino)phenyl]-1,3-butadienyl]-2-ethyl perchlorate, Molecular Probes, Eugene, Oreg.), the Red series dyes, among others, and combinations thereof. See, e.g., various Beckman Coulter catalogs; The Handbook of Fluorescent Probes and Research Products, $6^{th}$ Ed., R. P. Haugland, Molecular Probes, Eugene, Oreg. It should be noted that dyes exists that can be metachromatic in some circumstances and non-metachromatic in others. One of skill in the art should be readily able to select the appropriate dye for use in this compositions and method in view of the additional teachings contained herein.

Still other dyes suitable for use as a primary dye or additional primary dye in the methods and compositions of this invention include, without limitation, ethidium bromide (Sigma-Aldrich Corp., St. Louis, Mo.), propidium iodide (3,8-Diamino-5-(3-diethylaminopropyl)-6-phenyl-phenanthridinium iodide methiodide, Sigma-Aldrich Corp., St. Louis, Mo.), hexidium iodide (Molecular Probes, Eugene, Oreg.), dihydroethidium (Molecular Probes, Eugene, Oreg.), ethidium monoazide (Molecular Probes, Eugene, Oreg.), the Thiazole Orange™ dye (Becton Dickinson, Franklin Lakes, N.J.), among others, and combinations thereof. See, Shapiro et al., cited above.

The metachromatic or non-metachromatic primary dye(s) of the compositions or method may be either a cell permeant Dye(s) or cell impermeant dye (s). By the term "cell permeant" is meant to describe a dye that readily penetrates a cell wall and stains the components of the same without requiring the additional presence of a permeabilizing agent.

Typically, cell-permeant dyes are utilized to stain live cells or components of cells that have not been lysed. Preferably, cell permeant dyes are utilized to analyze samples containing whole blood. Thus, in the compositions and methods of this invention, where the primary dye is cell permeant, the composition or method may optionally employ a cell permeabilizing agent to enhance permeability of the cell to the dye. However, in compositions and methods of this invention, where the primary dye is cell impermeant, the composition or method does employ a cell permeabilizing agent to allow the impermeant dye to enter permeate the cell wall and bind to its targets therein.

In yet a further embodiment, the primary dye can be selected from among intercalating dyes. As used herein and throughout the specification, the phrase "intercalating dye" is meant to describe a dye that intercalates between the nucleic acid molecules. The intercalating dye can intercalate between the nucleic acid molecules of RNA and single and double stranded DNA. Preferably, the molecular configuration of the intercalating dye is planar. Alternatively, the primary dye(s) can be a non-intercalating dye. As an example, intercalating primary dyes include propidium iodide or Thiazole Orange dye. Still another embodiment of this invention employs a primary dye that is intercalating and a second primary dye that is not intercalating.

B. The Second Dye or Blocking Agent

The composition of the invention further includes a non-intercalating dye or reagent which competes with the primary dye for binding to the nonspecific binding sites in the cell. Thus, this component blocks non-specific interaction of the primary dye with the cell or cellular components. Typically, the blocking agent competes with other dyes present in the composition for the binding sites on the cells being analyzed. More typically, the blocking agent competes with low affinity dyes for specific binding sites on the cells. By doing so, nonspecific binding of the other components, i.e., the other dye or dyes, present in the composition is reduced or eliminated. The blocking agent can itself be a dye; in such circumstances, the dye is selected so that it is differentially detectable from the primary dye and any other dye components. Alternatively, the blocking agent may be any compound which blocks non-specific interactions of the primary dye without affecting the specific binding of the primary dye to its target(s).

Suitably, a blocking agent is either non-fluorescent, or is selected from among dyes that fluoresce at wavelengths different from the wavelength of the primary dye(s) in the composition. Preferably, the blocking agent is non-fluorescent at the wavelength that activates fluorescence of the primary dye. In one embodiment, the blocking agent fluoresces at a wavelength equal to or less than the wavelength of the excitation laser used to fluoresce the sample. In another embodiment, the wavelength is equal to or less than about 488 nm.

In one embodiment, the blocking agent is a non-intercalating dye. Preferably, the non-intercalating dye is a DNA-specific dye. As used herein and throughout the specification, the term "non-intercalating DNA-specific" is meant to describe a dye that binds externally to DNA. Preferably, the non-intercalating dye is not affected by DNA condensation and has a strong preference for A-T base pairs and minor grooves of DNA. Selection of a non-intercalating dye is particularly desirable in compositions containing primary dyes that are intercalating dyes. However, such non-intercalating dyes can be utilized as blocking agents in compositions of the invention that contain primary dyes which are non-intercalating.

A number of suitable blocking agents are known in the art and can be readily utilized in the compositions of the invention, including, without limitation, bisbenzamide (N,N'-(dithiodi-2,1-phenyl)-bisbenzamide, Sigma-Aldrich Corp., St. Louis, Mo.), the Hoechst 33258™ dye (bisbenzimide, 2'-(4-hydroxyphenyl)-5-(4-methyl-1-peperazinyl)-2,5-bi-1H-benzimidazole trihydrochloride pentahydrate; Molecular Probes, Eugene, Oreg.), the Hoechst™ 34580 dye (Molecular Probes, Eugene, Oreg.), the Hoechst 33342™ dye (bisbenzimide, 2'-(ethoxyphenyl)-5-(4-methyl-1-peperazinyl)-2,5-bi-1H-benzimidazole trihydrochloride trihydrate; Molecular Probes, Eugene, Oreg.), 4',6-diamidino-2-phenyl-indole dihydrochloride (DAPI, Molecular Probes, Eugene, Oreg.), 4',6-bis-[2-imidazoxolinyl-4H, 5H]-2-phenyl-indole (DIPI, Molecular Probes, Eugene, Oreg.), the Eosin™ Y dye (Sigma-Aldrich Corp., St. Louis, Mo.), the Orcein™ dye (Sigma-Aldrich Corp., St. Louis, Mo.), the Phloxine™ B dye (2',4',5',7'-tetrabromo-4,5,6,7-tetrachlorofluorescein disodium salt, Sigma-Aldrich Corp., St. Louis, Mo.), the Pentoxiphilline™ dye (Sigma-Aldrich Corp., St. Louis, Mo.), the Quinacrine™ dye (6-chloro-9-(4-diethyl-1-methylbutylamino)-2-methoxyacridine dihydrochloride, Sigma-Aldrich Corp., St. Louis, Mo.), among others, and combinations thereof.

Although a limited number of blocking agents have been described in the literature, the art is devoid of any suggestion that the combination of these blocking agents can be combined with a primary dye in a single composition which provides satisfactory differential fluorescence. More particularly, it is the inventors' discovery that the use of a substantial excess of blocking agent is required in order to out-compete other dyes for the weak binding sites, thereby increasing the binding of both dyes to the strong-binding sites in the cells, i.e., increasing specific binding relative to non-specific binding.

The excess of blocking agent utilized in the present invention is dependent upon the speed at which staining is needed. Typically, if it is necessary to stain the sample is a short amount of time, more blocking agent is needed. Alternatively, if it is not necessary to stain the sample in a short amount of time, less blocking agent can be utilized. Preferably, the blocking agent is present in the composition in a substantial excess of the other components in the composition. More preferably, the blocking agent is present in an at least 20-fold molar excess, i.e., an at least 20:1 molar ratio of blocking agent to primary fluorescent dye. Even more preferably, the blocking agent is present in an at least about 20 to about 500-fold molar excess, i.e., about 20:1 to about 500:1 molar ratio of blocking agent to primary fluorescent dye.

In still another embodiment, the blocking agent is present in an at least 20-fold molar excess, i.e., an at least 20:1 molar ratio of blocking agent to primary fluorescent dye. For other embodiments, the blocking agent is present in at least a 100-fold molar excess, i.e., a 100:1 molar ratio of blocking agent to primary fluorescent dye. In still other embodiments, the blocking agent is present at a 150-fold molar excess, i.e., a 150:1 molar ratio of blocking agent to primary fluorescent dye.

The selection of a the combination of a suitable primary dye with a suitable blocking reagent for use in the methods of this invention may employ simple experimentation and is well within the knowledge of the art. As one embodiment, an experiment employs normal human RBCs as a negative control that contains cell membrane and hemoglobin (no DNA or RNA sample) and avian RBCs which have a nucleus. After exposure to a conventional lytic agent, the avian RBCs are lysed, leaving only cell membrane and DNA (DNA sample). A third sample is prepared by conventionally chemically attaching RNA to human RBC, thereby providing a sample containing cell membrane, hemoglobin and RNA (RNA sample). A first primary dye is selected from among known fluorescent, preferably metachromatic dyes. Thereafter, a second blocking reagent is selected for its ability to bind DNA and its similarity in structure, e.g., in planar orientation, change etc, to the primary dye. Various concentrations of primary dye and blocking reagent are introduced into the three test samples according to a ratio of blocking reagent to dye of greater than 20:1 and the samples are analyzed by flow cytometry to determine if any combination permits differential staining between the three samples. In this manner, a suitable primary dye, blocking reagent composition may be selected without undue or complicated experimentation according to this invention.

A variety of different combinations of dyes and blocking agents will thus be readily apparent to one of skill in the art. For example, in one embodiment, a composition for staining cells is provided which contains a primary fluorescent dye and a non-fluorescent blocking agent. The molar ratio of the blocking agent to the primary fluorescent dye is at least about 20:1.

C. The Permeabilization Reagent

In still other embodiments, the compositions of the invention include a permeabilization or cell permeabilizing agent with the dyes in the ratios above defined. In some embodiments, a first permeant dye is mixed with a permeabilizing reagent in the absence of the second dye. Typically, in order to effect rapid uptake of the dyes, the composition of the invention is formulated to contain a non-lytic permeant enhancer, i.e., a permeabilization reagent or sphering reagent, which may be readily selected by one of skill in the art. Surprisingly, when combined with a cell permeant first dye, the permeabilizing agent enhances the dye function.

As used herein, the phrase "rapid uptake" refers to the ability of molecules to cross a cell membrane within the time frame that is desirable for automated flow cytometry. Generally, rapid uptake indicates that the dye molecules, when using the compositions of the invention, permeate a cell membrane in less than about 5 minutes, preferably less than about 1 minute, and most preferably less than about 30 seconds. However, one of skill in the art can adjust this time as needed as desired, e.g., by increasing incubation time to 90 second or decreasing incubation time, e.g., to about 30 seconds.

Thus, the compositions of the present invention permit steady state kinetics to be obtained, thereby indicating that the rapid fluorescent dye uptake, as measured by fluorescent intensity, is linear over the analysis interval of greater than five minutes and that the primary dye/blocking agent composition reaches equilibrium more efficiently and faster than compositions which do have contain a blocking agent.

In one embodiment, the non-lytic permeant enhancer is a zwitterionic surfactant or zwittergent which isovolumetrically spheres the reticulocytes and red blood cells within a blood sample. Such enhancers can be used with both permeant and non-permeant dyes and are typically utilized to analyze red blood cells and reticulocytes. Typical isovolumetric sphering reagents can be selected by one of skill in the art and include, without limitation, anionic surfactants including ammonium perfluoralkyl carboxylate (commercially available as Fluorad™ FC-143, 3M Company, St. Paul, Minn.), sodium lauroyl myristoyl lactylate (commercially available as Pationic™ 138C, R.I.T.A Corp, Woodstock, Ill.); non-ionic surfactants including Dodecyl-β-D-maltoside, N,N-bis-[3-D-gluconamidopropyl) cholamide, polyoxypropylene-polyoxyethylene block copolymer, N-Tetradecyl-β-D-maltoside, Daconyl-N-methyl-glucamide, n-Dodecyl-β-D-glucopyranoside, n-Decyl-β-D-glucopyranoside, polyethylene glycol ester of stearic acid, ethoxylated cocomonoglyceride, octyphenoxypoly(ethyleneoxy)ethanol, ethoxylated octylphenol, and linear alcohol, or, from among the cationic surfactants, coco hydroxyethyl imidazoline, lauryltrimethylammonium chloride, decyltrimethylammonium bromide, octyltrimethylammonium bromide, or from among the zwitterionic surfactants lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosulfobetaine, N-dodecyl-N,N-dimethyl-3-ammonio-1-propanesulfonate, and N-tetradecyl-N,N-dimethyl-3-ammonio-1-propanesulfonate.

The concentration of the permeabilizing agent or sphering reagent in the composition ranges from about 3 µg/mL to about 40 µg/mL. In another embodiment the range of permeabilizing agent in the composition to effectively isovolumetrically sphere reticulated cells and RBCs within a blood sample ranges from about 15 to 25 µg/mL. The osmolality of the composition preferably ranges from about 250 to about 350 mOSm to effectively enable isovolumetric sphering. See, for example, the concentration and osmolality values noted in U.S. Pat. No. 6,060,322. Such concentrations and osmolality are readily available in the art. However, one of skill in the art could readily adjust the concentration and osmolarity as needed or desired to isovolumetrically sphere the cells using salts and other osmotically active agents. Suitable osmolality agents include mono-, or divalent alkali salts that do not precipitate or react adversely with the dyes in the composition.

As stated above, such permeabilizing agents may be used in compositions in which the dyes and blocking agents are themselves permeant to the cell wall. In compositions in which the primary dye(s) and/or the blocking reagent is impermeant, such permeabilizing agents are required in the compositions.

D. Other Components of the Composition

Additional components can be added to the composition of the invention. For example, buffers or solvents can be employed in situations where maintaining the pH of the composition is necessary. Preferably, when a non-lytic permeabilizing agent is included in the composition of the invention, the pH of the dye composition is maintained at a physiological pH range of about 5 to about 7.5. Alternatively, when a lytic reagent is included the composition of the invention, the pH is maintained at a pH of about 3 to about 8. The buffer can be selected from a variety of buffers known to those of skill in the art to be used in the compositions of the invention and include, without limitation, phosphate buffered saline (PBS) or isotonic saline, such as the ISOTON® II buffer (Beckman Coulter, Inc., Miami, Fla.) in U.S. Pat. No. 3,962,125, or the like. Additionally, such buffers can also be used to adjust the concentration of one or more of the components of the composition of this invention.

Preservatives can also be added to the compositions of the invention, and can be selected from, but are not limited to, 5-Chloro-2-methyl-4-isothiazolin-3-one and 2-methyl-4-isothiazolin-3-one (commercially available as ProClin™ 300 and ProClin™ 150, Sigma-Aldrich Corp., St. Louis, Mo.).

Suitable surfactants can also be included in the composition of the invention and are readily selected by one of skill in the art. In one embodiment, the compositions include a detergent and a second surfactant that also functions as a sphering agent for a cell. In another embodiment, the compositions can be designed to include a single surfactant functions as both a detergent and sphering agent. In yet a further embodiment, the composition can contain a single surfactant that provides the necessary surfactant function, but no sphering reagent function is required.

A detergent can also be included in the composition of the invention. Detergents can be readily selected from among non-ionic detergents. Desirably, these detergents are used at a concentration between about 0 to about 1%. In one embodiment of the invention, the detergents are used at concentrations of between about 0.001% to about 0.1%. Examples of suitable detergents include, octypenoxypoly(ethyleneoxy)ethanol (commercially available as Igepal CA630, N-6507, Sigma-Aldrich Corp., St. Louis, Mo.) or Nonidet P-40, Sigma-Aldrich Corp., St. Louis, Mo.), ethyoxylated octylphenol (commercially available as Triton X-100, T9284, Sigma-Aldrich Corp., St. Louis, Mo.), and linear alcohol alkoxylates (commercially available as Plurafac A-38 or Plurafac A-39, BASF Corp., Ludwigshafen, Germany). Other suitable detergents can be readily selected by one of skill in the art. Typically, these detergents are mixed with a sample (or vice versa), e.g., 1 to 2 $\mu$l of whole blood or the like, or separately formulated into a composition of the invention.

Additionally, sulfonic acids, or salt thereof, can be included in the composition of the invention. Some examples of such salts are commercially available, e.g., from Sigma-Aldrich (*Biochemicals and Reagents for Life Science Research*, Sigma-Aldrich Corporation, 2002).

The compositions of this invention may also contain a selected solvent. As defined herein, a solvent is meant to describe any liquid that can dissolve a solid, liquid, or gas. Suitable solvents for preparation of the components of this invention include, without limitation, water-based or miscible liquids, such as dimethylsulfoxide (DMSO), methanol, ethanol, and mixtures thereof. Selection of a suitable solvent is however not a limitation on the present invention.

The desirability of including the various optional components is readily determined by one of skill in the art, taking into consideration such factors as the dyes and blocking agent selected, storage conditions, and the like.

E. Selected Compositions of the Invention

In one embodiment, a composition for staining cells is provided which contains a first fluorescent dye and a second dye that fluoresces at a wavelength different from the wavelength of the first dye and reduces nonspecific binding of the first dye, wherein the molar ratio of said second dye and said first dye is at least about 20:1. Preferably, the blocking agent is the Hoechst™ 33258 blocking agent or Hoechst 33342™ blocking agent. The first dye can be a metachromatic dye, a non-metachromatic dye, a cell-permeant dye, an intercalating dye, or any combination thereof, selected from the lists above. A preferred primary dye is Acridine Orange.

In another embodiment, a composition for staining cells is provided containing a metachromatic fluorescent dye, such as Acridine Orange, and a second blocking dye that fluoresces at a wavelength different from the wavelength of the metachromatic dye and reduces nonspecific binding of the metachromatic dye, wherein the molar ratio of said second dye and the metachromatic dye is at least about 100:1. The second dye/blocking agent is the Hoechst™ 33258 blocking agent or Hoechst 33342™ blocking agent. Optionally this compositions contains a permeabilizing reagent. For example, such a composition contains one ml sphering reagent, 2 $\mu$l of a 1 mM solution of Acridine Orange and 10 $\mu$l of Hoechst 33258 reagent. This composition is suitable for addition to a 2 $\mu$l sample of, for example, whole blood. See the examples below.

In a further embodiment, a composition for staining cells is provided containing a non-metachromatic dye and a second dye/blocking agent that fluoresces at a wavelength different from the wavelength of the non-metachromatic dye and reduces nonspecific binding of the metachromatic dye, wherein the molar ratio of said second dye and said non-metachromatic dye is at least about 100:1.

In yet another embodiment, a composition for staining cells is provided containing a fluorescent cell permeant dye and a second dye that fluoresces at a wavelength different from the wavelength of the cell permeant dye and reduces non-specific binding of the cell permeant dye, wherein the molar ratio of said second dye and said cell permeant dye is at least about 100:1.

In still a further embodiment, a composition for staining cells is provided which contains the Acridine Orange dye and the Hoechst™ 33258 blocking agent, where the molar ratio of the Hoechst™ 33258 blocking agent to the Acridine Orange dye is about 100:1. As demonstrated by the examples below, although AO and these Hoechst dyes bind DNA in a different manner, they are still competitive. When tested with washed permeabilized avian red cells (a DNA reference material), a composition of this invention containing Hoechst 33258 dye and AO at a 100:1 ratio, reduces ~526 nm fluorescence attributed to AO alone by more than 75%. Similarly a composition of this invention containing the Hoechst 33342 dye and AO at a ratio of 100: reduces ~526 nm fluorescence attributed to AO alone by more than 50%. Thus, the presence of the blocking dye, that is not excited fluorescently by the 488 nm laser, in molar excess of the fluorescently excited primary dye AO improves the specificity and fluorescent discrimination of the fluorescent primary dye. This is achieved by the reduction of non-specific binding and fluorescence of the primary dye that would have occurred without the blocking reagent. A further unexpected result of the combination is that H33258 blocking reagent at high concentrations has been shown to produce increased light scatter (>15 degrees) due to condensation and precipitation of the nuclear proteins and the polynucleotide complex. This produces an effect of an increase in the internal index of refraction of the cells due to the presence of the H33258 complex. This effect is not observed in the compositions containing AO. Thus the compositions of this invention in addition to improving the primary dye's metachromatic separation, also enhances light scatter discrimination of various cell types.

Still another combination of this invention employs the above combination of Hoechst 33258 dye and AO, with an additional dye that stains acidophilic granules, e.g., Neutral Red.

Yet another combination of this invention employs the above combination of Hoechst 33258 dye and AO, with an additional dye that stains basophilic granules, e.g., Basic Orange 21.

In another embodiment, a combination of this invention employs the above combination of Hoechst 33258 dye and AO, with an additional dye that stains cellular membranes, e.g., DiOC.

In another embodiment, a cell permeant first dye, such as AO or TOTO dyes is formulated with the cell permeabilizing reagent.

It will be readily apparent to one of skill in the art that many other desirable compositions of the invention may be described taking into consideration the above description of the components. Such a combination has the advantages of improving scatter characteristics, when excited with a laser at the primary dye excitation wavelength (e.g., 488 nm for AO), reducing nonspecific fluorescent binding of the primary dye, and improved fluorescent peak separation characteristics. The effect of the blocking dye on the intense nuclear emission staining of the primary dye (e.g., the 526 nm emission staining of AO) reduces spectral overlap into the red emission of the primary dye bound to RNA or granules. This reduction in DNA staining enhances discrimination of DNA condensation. The presence of the blocking dye causes condensation and precipitation of nuclear associated proteins, enhancing cell separation based on non-fluorescent light scatter. The combination of the blocking dye and the primary dye(s) for nonspecific binding sites improves the signal to noise value of dye fluorescence and allows rapid kinetic equilibrium binding of the primary dye(s).

E. Preparation of Compositions of the Invention

The dyes and optional non-lytic permeant enhancer can be dissolved in an appropriate solvent to form mixtures or solutions. For storage, typically a relatively high concentration of the dye is dissolved in a suitable solvent to obtain a stock solution. Preferably, the dye(s) are dissolved in the solvent at a total dye concentration ranging up to the saturation point of the dye(s). Such concentrations may be readily selected by one of skill in the art.

The stock solution can be diluted in other reagents or buffers, including, for example, water, saline, phosphate buffered saline (PBS), or isotonic saline. The final dye concentration in such compositions can be varied depending on the application. In one embodiment, the concentration of the dye in the final composition added to a sample of about 2 $\mu$l of whole blood is in the range of about 1 to 5 $\mu$l of a 1 mM solution, more preferably about 2 $\mu$l of that solution should be adequate. However, selection of an appropriate concentration or diluting solvent is not a limitation on the present invention. Other concentrations may be selected by the person of skill in the art.

Suitably, the compositions of the invention are prepared by combining the dyes, blocking agents, and any optional components added, using standard mixture techniques.

II. Methods of the Invention

The composition and methods of the invention can be utilized for a variety of purposes. One embodiment of this invention is the use of the composition for staining, detection, and analysis of cells in a suitable biological sample. The cells can be obtained from a variety of hosts and can include mammalian cells, including human cells. Most preferably, the cells include human cells. However, one of skill in the art will readily understand that use of the dye compositions of the present invention are not limited to cell type. Advantageously, the dyes, methods and compositions of the invention do not require cell fixation and are therefore particularly well suited for use in analyses of living cells. However, selection of the cell population is not a limitation on the present invention.

Thus, typical biological samples include whole blood, plasma, saliva, urine, other biological secretions and excretions, and laboratory preparations containing cells, e.g., cells in buffers, saline, etc. Suitable samples, e.g., those containing reticulocyte cell populations for analysis, may be selected from whole blood or blood samples that have been enriched or depleted by certain additional processes prior to staining with the compositions of this invention. Such enrichment or depletion processes can include, among others, centrifugation, ficoll assisted gravity separation or magnetic separation. Such samples can also be treated with RNAse and DNAse or as necessary. Alternatively, the samples can be washed to remove lysed cells.

Any cells having cellular components including nucleic acids can be analyzed using the compositions of the invention. Preferably, the cells that can be analyzed include, without limitation, red blood cells (RBC), white blood cells (WBC), classes of WBC including lymphocytes, blast cells, nucleated RBCs, basophils, mast cells, neutrophils, monocytes, eosinophils, reticulocytes, and combinations thereof. The cellular components of the cells that can be analyzed also include, without limitation, RNA, DNA, acidophilic granules, basophilic granules, red blood cell inclusions, and intracellular parasites, including, e.g., viruses, among others.

The compositions and methods of this invention are thus useful for platelet and white blood cell (WBC) analysis, maturation, WBC identification, reticulocyte hemoglobin analysis, and red blood cell (RBC) inclusions. Further, the compositions are highly successful and reliable in reticulocyte analysis.

In another embodiment, the composition of the invention is useful in staining nucleic acids, including DNA and RNA. In samples containing free nucleic acids, e.g., nucleic acids not surrounded by an intact cell membrane of a cellular or non-cellular source, the composition of the invention can stain the nucleic acids. In one embodiment of the invention, a method is provided for contacting a sample containing nucleic acids with the composition of the invention.

In a further embodiment, the composition of the invention is suited for use in the detection and enumeration of reticulocytes, which contain RNA. The method of the invention therefore involves contacting a sample containing cells having reticulocytes with a composition of the invention.

In yet another embodiment, the composition of the invention is used to identify cellular components including, without limitation, lymphocytes, monocytes, neutrophils, cosinophils, and basophils.

In another embodiment, the composition of the invention can be utilized to facilitate rapid staining of cells. Typically, the method of the invention permits staining in about 5 minutes or less. Preferably, the method of the invention can permit staining in about 1 to about 60 seconds, about 5 seconds to about 45 seconds, about 4 to about 5 seconds, and about 10 to about 40 seconds. Preferably, reticulocytes are stained in less than about 10 to about 30 seconds and white blood cells are stained in less than about 5 minutes.

The method of the present invention, regardless of its particular intention and the cells or components to be identified, enhances differential staining of RNA, DNA and granules in a selected sample containing cells. The method involves staining cells in the sample by contacting the sample with a composition of the invention, optionally a sphering agent and/or solvent. The method may optionally include a step of permeabilizing the cells to penetration of dyes prior to contacting the sample with the composition of this invention. For example, a permeabilizing agent, such as those identified above may be admixed with the sample prior to contact with the dye-containing composition of the invention. This step may be used regardless of whether the composition itself contains a permeabilizing agent. After admixture of the sample with the composition of the invention, the mixture is then incubated for a suitable period of time, e.g., in one embodiment of the method of the invention, the dye composition is incubated with the selected sample for about 1 second to about 5 minutes.

Preferably, the dye composition is incubated with the sample for about 1 second to about 1 minute. However, if desired for purposes of convenience, this incubation period can be either extended or shortened. In another embodiment, incubation time is completely eliminated (i.e., 0 seconds). Desirably, this mixing and incubation can be performed at room temperature. Preferably, temperatures of about 20° C. to about 40° C. are utilized. More preferably, temperatures of about 22° C. to about 27° C. are utilized.

Cells stained with the dyes, according to the method of the invention, are then analyzed to detect differential expression of the RNA, DNA and granules in the sample. Such analytic methods include preferably enumeration and detection in an automatic flow cytometer or conventional hematology analyzer. However, these stained cells can also be counted by a manual procedure or automated microscopy. Automatic flow cytometers are well known in the art, and the present invention is not limited to the use of any particular flow cytometer. Such flow cytometers include, but are not limited to, the COULTER® XL™, HmX™, Gen*S™, LH750™, LH755™, and ReticONE™ flow cytometers (Beckman Coulter, Inc., Miami, Fla.), the SYSMEX-RAM1™ 9500, SF-3000, XE2100, and XE2100-L hematology analyzers (Sysmex Corporation of America, Long Grove, Ill.), the CELL-DYN™, 3200, 3700, and 4000 hematology analyzers (Abbott Laboratories, Abbott Park, Ill.), the PENTRA™ 60 and 120 Retic hematology analyzers (ABX Diagnostics, Montpellier Cédex, France), and the ADVIA™ 70 and 120 hematology analyzers (Bayer Diagnostics, Tarrytown, N.Y.), among others.

Different analytical techniques can be employed in the enumeration of reticulocytes via flow cytometric measurements including, but not limited to light scatter (forward, side and back), fluorescence, polarized fluorescent light discrimination, polarized scattered light discrimination, optical absorption, axial light loss, direct current (DC) electrical impedance, and radio frequency (RF) conductivity. In one embodiment of the invention, in using such flow cytometers, light scatter gates are used to isolate red cells, and fluorescent gates are then used to delineate reticulocytes from mature red cells and enumerate the reticulocytes. In a further embodiment, using flow cytometers, DC and light scatter light scatter gates are used to isolate red cells, and fluorescent gates are then used to delineate reticulocytes from mature red cells and enumerate the reticulocytes. In yet another embodiment of the invention, using flow cytometers, DC and fluorescent measurement alone are used to delineate reticulocytes from mature red cells and enumerate the reticulocytes. See, Peebles et al., 1981 *Am. J. Clin. Pathol.* 76:713–717; Davis et al., 1994 *Am. J. Clin. Pathol.*, 102:486–487; "Flow Cytometric Reticulocyte Quantification in the Evaluation of Hematologic Recovery". Spanish Multicentric Study Group for Hematopoietic Recovery. 1994 *Eur. J. Hematol.,* 53(5): 293–297; and U.S. Pat. Nos. 4,957,870 and 4,971,917.

A variety of lasers are known to those of skill in the art that can be utilized as the excitation sources for the flow cytometers. The lasers can be selected from, but are not limited to, argon, helium-neon, diode, and diode pumped solid-state lasers, depending upon the excitation wavelength of the dye of the invention selected for detection of reticulocytes. Selection of suitable light sources, and appropriate excitation wavelengths, are not a limitation on the present invention.

Suitable excitation wavelengths can be readily determined by one of skill in the art. Examples of suitable excitation wavelengths in the red spectral range include those in the range of 600 nm to 725 nm, and preferably 630 nm to 670 nm. See also the following examples. Other suitable excitation sources and wavelengths can be readily selected by one of skill in the art, taking into consideration the dye selected for use in the method and compositions of the invention.

In one embodiment, a method for analyzing cells is provided including contacting a sample containing cells with a composition of the invention as above described and analyzing the sample to detect the cells.

In another embodiment, the method for enhancing differential staining may involve separate steps. For example, a sample containing cells may be first contacted with one of the above-described blocking reagents (e.g., a second dye that fluoresces at a wavelength different from the wavelength of the primary dye) at an at least 20 molar excess to the primary dye. Separately thereafter, the sample may be contacted with the selected primary dye. The first contacting step allows the blocking reagent to bind sites to which the primary dye would ordinarily nonspecifically bind (or bind with low affinity). The second step allows the primary dye to bind only to sites to which it specifically binds with high affinity. Even performed in this way, the method reduces nonspecific binding of the primary dye. This method may optionally include an initial permeabilization step. Finally, the sample is analyzed as described herein for differential staining of the cell types and/or cellular components in the sample.

In a further embodiment, a method for analyzing reticulocytes, is provided including contacting a sample containing reticulocytes with a composition of the invention and analyzing the sample to detect the reticulocytes.

In yet another embodiment, a method for facilitating rapid transport of dye molecules through a cell membrane is provided including contacting a sample with a composition of the invention to form a mixture and incubating the mixture.

In a further embodiment, a method for enhancing binding of a dye to one component of a cell is provided including contacting a sample containing cells with a composition of the invention, wherein the second dye reduces nonspecific binding of the first dye to a second component of the cell.

III. Kits of the Invention

The present invention also includes kits for research or pharmaceutical or diagnostic medical use. For use in diagnostic assays and kits, the above-described primary dye(s) and blocking reagents are preferably included with suitable solvents, buffers, preservatives, and permeabilizing agents, as described above.

Also useful in such kits are antibodies to other binding sites on desired target cells or cell types, such as to cell surface determinants on WBC. Such antibodies may be associated with a detectable label that is capable, alone or in concert with other compositions or compounds, of providing a detectable signal. Where more than one antibody is employed in a diagnostic method, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength.

Other label systems that may be utilized in the methods of this invention are detectable by other means, e.g., colored latex microparticles (Bangs Laboratories, Indiana) in which a dye is embedded may be used in place of enzymes to form conjugates with the inhibitor sequences or ligands and provide a visual signal indicative of the presence of the resulting complex in applicable assays. Still other labels include fluorescent compounds, radioactive compounds or elements. Preferably, each reagent or ligand is associated with, or conjugated to a fluorescent detectable fluorochromes, e.g., fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art.

Detectable labels for attachment to antibodies and substrates useful in diagnostic assays of this invention may be easily selected from among numerous compositions known and readily available to one skilled in the art of diagnostic assays. The reagents and ligands of this invention are not limited by the particular detectable label or label system employed.

Methods for coupling or associating the label with an antibody are similarly conventional and known to those of skill in the art. Known methods of label attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995). Thus, selection of the label and coupling methods do not limit this invention.

For convenience, the conventional reagents for high throughput assays or other diagnostic assays useful according to this invention may be provided in the form of kits. Such kits are useful for evaluating blood samples for purposes of determining disease states associated with inappropriate types or numbers of blood cells, blood cell types or components thereof. Thus, such a kit will be useful in conducting the diagnostic assays discussed herein, e.g., in determining the status of treatment of an illness characterized by inappropriate cell type expression in a blood sample. Such a diagnostic kit contains the dyes, blocking agents, permeabilizing agents and other components of compositions of this invention. Such kits also contain labels, exemplified above, pre-attached to the other components of the specific assay to be performed, or provided separately for attachment to a selected component, e.g., a substrate. Alternatively, such kits may contain a simple mixture of such compositions or means for preparing a simple mixture.

The kits also include instructions for performing the particular assay, microtiter plates to which the components of the compositions of the invention have been pre-adsorbed, various diluents and buffers, labeled conjugates for the detection of specifically bound compositions and other signal-generating reagents, such as enzyme substrates, cofactors and chromogens. Other components may include indicator charts for calorimetric comparisons, disposable gloves, decontamination instructions, applicator sticks or containers, and a sample preparator cup.

Such kits provide a convenient, efficient way for a clinical laboratory to screen blood samples or other biological samples containing cells according to this invention.

One of skill in the art may be expected to vary the components of these diagnostic kits in obvious ways based on the knowledge in the art coupled with this disclosure. Such varied components are included in this embodiment of the invention.

EXAMPLES

These examples demonstrate the use of the compositions of the invention to analyze samples and detect cells. The data reported in these Examples demonstrates that the compositions and methods of this invention are useful in current instrumentation and methodologies and have performance parameters that permit improved hematopoietic analysis of samples. These examples are illustrative and do not limit the scope thereon. One of skill in the art will appreciate that although specific reagents and conditions are outlined in the following examples, modifications as described above can be made to provide the compositions of this invention or processes for use thereof.

Example 1

This example provides a comparison of a composition of the present invention, with dyes known in the art for the enumeration and maturity staging of red blood cell reticulocytes. Specifically, a composition of the present invention was compared to existing reticulocyte enumeration methods using known hematology and flow systems and dyes.

Fifteen (15) specimens of whole blood from normal donors and forty three (43) patient specimens from various local hospitals were collected for a total of fifty eight (58) whole blood specimens. After incubation, each sample was analyzed for the % reticulocytes. An estimated reticulocyte count was determined for each specimen using a LH750™ Beckman Coulter, Inc. hematology using standard techniques known in the art and the results were reported in Table 1. A range of 0.00% to 27.1% reticulocytes was obtained and the results organized into three categories (low, normal and high) based on the percent of reticulocyte present in the sample. Specifically as defined in Table 1, a reticulocyte count of less than about 0.9% reticulocytes indicated a low reticulocyte count; a reticulocyte count of about 0.9% to about 2.0% reticulocytes indicated a normal reticulocyte count; and a reticulocyte count of greater than about 2.0% reticulocytes indicated a high reticulocyte count.

TABLE 1

| % Reticulocytes | \multicolumn{9}{c}{Day} | TOTAL Specimens |
|---|---|---|---|---|---|---|---|---|---|---|
| | 1 | 2 | 3 | 4 | 5 | 6 | 7 | 8 | 9 | |
| | \multicolumn{9}{c}{Number of Specimens} | |
| Low | 1 | 5 | 1 | 1 | 2 | 1 | 0 | 0 | 0 | 11 |
| Normal | 1 | 1 | 4 | 2 | 2 | 0 | 0 | 0 | 1 | 11 |
| High | 8 | 2 | 4 | 6 | 4 | 0 | 3 | 5 | 4 | 36 |
| | | | | | | | | | | 58 |

Once the samples were grouped according to the estimated % reticulocyte count as generated by the hematology analyzer, the samples were then analyzed for a more exact reticulocyte and immature reticulocyte fractions (IRF) counts using a composition of the present invention and dyes currently utilized in the art, such as those shown in Table 2.

TABLE 2

| Dye | Cytometer |
|---|---|
| Auramine ™ O stain | Sysmex ™ RAM-1 |
| CD4K530 Cyanine ™ dye | the Cell Dyne ™ 4000 |
| Methylene Blue ™ dye | Beckman Coulter LH 750 ™ |
| ReticONE ™ dye | Beckman Coulter XL-MCL ™ |

The IRF is a measurement of the distance between the lowest to highest RNA containing reticulocytes, with the reticulocyte measurement technique greatly influencing the IRF value. To determine the IRF of the sample, the following formula was utilized:

$$IRF = \frac{\text{\# of high fluorescent reticulocytes} + (\text{\# of mid-range fluorescent reticulocytes})}{\text{total reticulocytes}}$$

Additional measurements of reticulocyte counts were determined using the dyes in Table 3 using standard testing techniques. The results of these analyses are reported in Table 3, identified by the dye name.

To prepare a composition of this invention, about 2 µL of the sample of whole blood was combined with about 2 µL of a 1 mM solution of Acridine Orange (the primary dye), 1 ml of sphering agent (maltoside), and 10 µl of a 20 mM solution of Hoechst 33258 reagent. The sample mixture was incubated at room temperature for about 1–5 minutes. This mixture containing the composition of the present invention was then analyzed using the Beckman Coulter XL-MCL™ flow cytometer.

A. Samples Having Low Reticulocyte Counts

The following data was based on ten (10) separately prepared determinations of one of the above-noted samples having low reticulocyte counts. The ReticONE™, XL-MCL™ flow cytometry based system was based on nine (9) separately prepared determinations, which was due to volume constraints. Tables 3–4 report the % reticulocytes and % IRF, respectively, contained in the sample using the four dyes known in the art and composition of the invention. The data obtained were compared with the results obtained for the analysis of the Auramine™ O dye using the Sysmex™ RAM-1 flow cytometer.

Table 3 represents the results of replicate precisions of the sample on all test instruments and for all ranges, which include low, normal and high reticulocytes as defined above. The dye name over the column also represents the instrument identified with the dye as in Table 2 above.

TABLE 3

% Reticulocytes

| | Dye | | | | |
|---|---|---|---|---|---|
| Run | Composition of the invention | Methylene Blue ™ dye | Cyanine ™ dye | Auramine ™ O stain | ReticONE ™ dye |
| Run 1 | 0.52 | 0.182 | 0.581 | 0.74 | 1.47 |
| Run 2 | 0.53 | 0.281 | 0.501 | 0.6 | 1.53 |
| Run 3 | 0.61 | 0.141 | 0.515 | 0.56 | 1.07 |
| Run 4 | 0.51 | 0.229 | 0.558 | 0.79 | 1.38 |
| Run 5 | 0.62 | 0.337 | 0.513 | 0.69 | 1.27 |
| Run 6 | 0.56 | 0.264 | 0.522 | 0.68 | 1.19 |
| Run 7 | 0.48 | 0.189 | 0.558 | 0.66 | 1.12 |
| Run 8 | 0.51 | 0.253 | 0.468 | 0.61 | 1.14 |
| Run 9 | 0.62 | 0.434 | 0.573 | 0.58 | 1.18 |
| Run 10 | 0.61 | 0.305 | 0.523 | 0.67 | |
| Mean | 0.56 | 0.26 | 0.53 | 0.66 | 1.26 |
| 2SD | 0.11 | 0.17 | 0.07 | 0.14 | 0.33 |
| % CV | 956 | 32.49 | 6.68 | 11.00 | 12.94 |
| Min | 0.48 | 0.14 | 0.47 | 0.56 | 1.07 |
| Max | 0.62 | 0.43 | 0.58 | 0.79 | 1.53 |
| Max-Min | 0.14 | 0.29 | 0.11 | 0.23 | 0.46 |

TABLE 4

% IRF

| | Dye | | | | |
|---|---|---|---|---|---|
| Run | Composition of the invention | Methylene Blue ™ dye | Cyanine ™ dye | Auramine ™ O stain | ReticONE ™ dye |
| Run 1 | 0.12 | 0.237 | 0.071 | 0.132 | 0.058 |
| Run 2 | 0.11 | 0.187 | 0.049 | 0.076 | 0.056 |
| Run 3 | 0.09 | 0.239 | 0.103 | 0.099 | 0.079 |
| Run 4 | 0.10 | 0.216 | 0.105 | 0.082 | 0.087 |
| Run 5 | 0.08 | 0.211 | 0.112 | 0.103 | 0.08 |
| Run 6 | 0.08 | 0.174 | 0.102 | 0.048 | 0.061 |
| Run 7 | 0.09 | 0.164 | 0.146 | 0.104 | 0.062 |
| Run 8 | 0.12 | 0.232 | 0.129 | 0.102 | 0.08 |
| Run 9 | 0.08 | 0.199 | 0.123 | 0.139 | 0.057 |
| Run 10 | 0.09 | 0.182 | 0.078 | 0.126 | |
| Mean | 0.10 | 0.20 | 0.10 | 0.10 | 0.07 |
| 2SD | 0.03 | 0.05 | 0.06 | 0.06 | 0.02 |
| % CV | 16.76 | 13.26 | 28.47 | 27.27 | 17.87 |
| Min | 0.08 | 0.16 | 0.05 | 0.05 | 0.06 |
| Max | 0.12 | 0.24 | 0.15 | 0.14 | 0.09 |
| Max-Min | 0.05 | 0.08 | 0.10 | 0.09 | 0.03 |

These data illustrate that the composition of the present invention provided a good analysis of the % reticulocyte in the samples when compared to the Auramine™ O stain and also resulted in a lower % cell volume (% CV) as compared to the Auramine™ O stain.

These data also illustrate that the % IRF demonstrated similarities between the mean values of the Auramine™ O stain, the composition of the present invention, and the Cyanine™ dye. However, it is noted that the results obtained for the Methylene Blue™ dye and ReticONE™ dye differed from the composition of the present invention.

B. Samples Containing Normal Reticulocyte Counts

The following data was based on ten (10) separately prepared determinations of a sample having normal reticulocyte counts. Tables 5–6 report the % reticulocytes and % IRF, respectively, contained in the sample using the four dyes known in the art and composition of the invention. The data obtained were compared with the results obtained for the analysis of the Auramine™ O dye using the Sysmex™ RAM-1 flow cytometer.

TABLE 5

% Reticulocytes

| | Composition of the invention | Methylene Blue™ dye | Cyanine™ dye | Auramine™ O stain | ReticOne™ dye |
|---|---|---|---|---|---|
| Run 1 | 1.20 | 0.94 | 1.23 | 1.14 | 1.93 |
| Run 2 | 1.17 | 0.75 | 1.12 | 1.12 | 1.89 |
| Run 3 | 1.19 | 0.93 | 1.20 | 1.00 | 1.61 |
| Run 4 | 1.22 | 1.04 | 1.33 | 1.02 | 2.13 |
| Run 5 | 1.25 | 1.22 | 1.29 | 1.11 | 1.91 |
| Run 6 | 1.24 | 1.02 | 1.13 | 1.14 | 1.78 |
| Run 7 | 1.25 | 1.04 | 1.22 | 1.24 | 1.56 |
| Run 8 | 1.29 | 0.90 | 1.18 | 1.09 | 1.88 |
| Run 9 | 1.25 | 0.88 | 1.26 | 1.13 | 1.6 |
| Run 10 | 1.09 | 1.18 | 1.27 | 1.13 | 1.86 |
| Mean | 1.21 | 0.99 | 1.22 | 1.11 | 1.82 |
| 2SD | 0.11 | 0.28 | 0.14 | 0.13 | 0.36 |
| % CV | 4.55 | 14.15 | 5.53 | 6.01 | 9.85 |
| Min | 1.09 | 0.75 | 1.12 | 1.00 | 1.56 |
| Max | 1.29 | 1.22 | 1.33 | 1.24 | 2.13 |
| Max-Min | 0.19 | 0.47 | 0.21 | 0.24 | 0.57 |

TABLE 6

% IRF

| | composition of the invention | Methylene Blue™ dye | Cyanine™ dye | Auramine™ O stain | ReticOne™ dye |
|---|---|---|---|---|---|
| Run 1 | 0.27 | 0.31 | 0.183 | 0.143 | 0.076 |
| Run 2 | 0.25 | 0.26 | 0.184 | 0.131 | 0.094 |
| Run 3 | 0.30 | 0.26 | 0.191 | 0.118 | 0.08 |
| Run 4 | 0.26 | 0.25 | 0.184 | 0.179 | 0.058 |
| Run 5 | 0.22 | 0.24 | 0.226 | 0.144 | 0.076 |
| Run 6 | 0.25 | 0.23 | 0.184 | 0.142 | 0.084 |
| Run 7 | 0.24 | 0.23 | 0.196 | 0.126 | 0.092 |
| Run 8 | 0.25 | 0.21 | 0.157 | 0.18 | 0.056 |
| Run 9 | 0.25 | 0.27 | 0.19 | 0.129 | 0.086 |
| Run 10 | 0.23 | 0.26 | 0.216 | 1.167 | 0.081 |
| Mean | 0.25 | 0.25 | 0.19 | 0.15 | 0.08 |
| 2SD | 0.04 | 0.05 | 0.04 | 0.04 | 0.03 |
| % CV | 8.22 | 10.09 | 9.93 | 15.18 | 17.18 |
| Min | 0.22 | 0.21 | 0.16 | 0.12 | 0.06 |
| Max | 0.30 | 0.31 | 0.23 | 0.18 | 0.09 |
| Max-Min | 0.08 | 0.09 | 0.07 | 0.06 | 0.04 |

These data illustrate that the composition of the present invention provided a good analysis of the % reticulocyte in the samples as compared to the Auramine™ O stain and also resulted in a lower % CV and difference between the minimum and maximum reticulocyte values as compared to the Auramine™ O stain.

These data also illustrate that the % IRF demonstrated similarities between the means of the Methylene Blue™ dye, the composition of the invention, and the Cyanine™ dye. However, the mean obtained for the Auramine™ O stain was lower than the mean for the composition of the present invention. Further, the ReticONE™ dye had the lowest difference between the maximum and minimum reticulocyte values.

C. Samples Containing High Reticulocyte Counts

Due to the limited quantity of specimen available for the high reticulocyte analysis, the following data was based on ten (10) separately prepared determinations for the composition of the present invention, nine (9) determinations for the Auramine™ O stain, three (3) determinations for the Methylene BlUe™ dye, and one (1) determination was performed with the Cyanine™ dye. No samples were analyzed using the ReticONE™ dye. Tables 7–8 report the % reticulocytes and % IRF, respectively, contained in the sample using the five instruments noted above. Data was compared with the results as obtained for the Auramine™ O stain.

TABLE 7

% Reticulocytes

| | composition of the invention | Methylene Blue™ dye | Cyanine™ dye | Auramine™ O stain | ReticOne™ dye |
|---|---|---|---|---|---|
| Run 1 | 13.37 | 12.31 | 10.7 | 12.05 | |
| Run 2 | 13.57 | 12.19 | | 12.05 | |
| Run 3 | 13.22 | 12.6 | | 12.19 | |
| Run 4 | 12.93 | | | 11.74 | |
| Run 5 | 13.44 | | | 11.78 | |
| Run 6 | 13.53 | | | 11.88 | |
| Run 7 | 12.80 | | | 11.91 | |
| Run 8 | 12.87 | | | 12.19 | |
| Run 9 | 13.24 | | | 11.49 | |
| Run 10 | 12.62 | | | | |
| Mean | 13.16 | 12.37 | 10.70 | 11.92 | |
| 2SD | 0.67 | 0.42 | | 0.46 | |
| % CV | 2.53 | 1.71 | | 1.92 | |
| Min | 12.62 | 12.19 | 10.70 | 11.49 | 0.00 |
| Max | 13.57 | 12.60 | 10.70 | 12.19 | 0.00 |
| Max-Min | 0.96 | 0.41 | 0.00 | 0.70 | 0.00 |

TABLE 8

% IRF

| | Composition of the invention | Methylene Blue™ dye | Cyanine™ dye | Auramine™ O stain | ReticOne™ dye |
|---|---|---|---|---|---|
| Run 1 | 0.58 | | | 0.54 | |
| Run 2 | 0.58 | | | 0.54 | |
| Run 3 | 0.57 | | | 0.52 | |
| Run 4 | 0.60 | | | 0.52 | |
| Run 5 | 0.62 | | | 0.53 | |
| Run 6 | 0.62 | | | 0.53 | |
| Run 7 | 0.58 | | | 0.52 | |
| Run 8 | 0.71 | | | 0.50 | |
| Run 9 | 0.71 | | | 0.52 | |
| Run 10 | 0.72 | | | | |
| Mean | 0.63 | | | 0.52 | |
| 2SD | 0.12 | | | 0.02 | |
| % CV | 9.52 | | | 2.30 | |
| Min | 0.57 | 0.00 | 0.00 | 0.50 | 0.00 |
| Max | 0.72 | 0.00 | 0.00 | 0.54 | 0.00 |
| Max-Min | 0.15 | 0.00 | 0.00 | 0.04 | 0.00 |

These data illustrate that the composition of the present invention provided a higher analysis of the % reticulocyte in the samples when compared to the Auramine™ O stain. Without wishing to be bound by theory, this can reflect the specificity of the dyes of the present invention to allow for the reticulocyte cells to be better separated from the negative, mature red cell populations and allow for better enumeration.

These data also illustrate a higher mean and % CV of IRF when using the composition of the invention, which can be due to the specific staining characteristics of the compositions of the present invention.

Taken collectively, these data illustrate that the composition of the present invention was more effective in hematopoietic analysis.

Example 2

This example demonstrates that the composition of the present invention is more effective in determining the paired precision and reticulocyte parameter accuracy than the compositions and methods known in the art.

The composition of the present invention was prepared and the whole blood sample treated as described in Example 1. The % reticulocytes and % IRF were determined using the Beckman Coulter XL-MCL™ hematology analyzer.

The results obtained for the composition of the present invention were compared to results obtained using the Auramine™ O stain and the Sysmex™ RAM-1 hematology analyzer, and the Methylene Blue™ dye using the LH 750™ hematology analyzer.

A. Paired Precision

The paired precision was measured by determining the difference between the % reticulocytes and % IRF for Runs 1 and 2 in Table 9 using the composition of the present invention and the Auramine™ O stain.

TABLE 9

|  | Composition of the Invention | | Auramine ™ O | |
| --- | --- | --- | --- | --- |
|  | Reticulocytes | IRF | Reticulocytes | IRF |
| Mean Difference | −0.01 | −0.004 | 0.06 | −0.005 |
| SD of Difference | 0.28 | 0.067 | 0.36 | 0.028 |

These data demonstrate that the composition of the present invention is more effective in obtaining the mean difference and standard deviation of difference of % reticulocyte as compared to the Auramine™ O stain.

B. Reticulocyte Parameter Accuracy

Reticulocyte parameter accuracy was measured by determining the sum of the variables of precision using samples having about 0.00 to about 30% reticulocytes, i.e., low, normal and high range reticulocyte samples. The mean difference for each composition was calculated by subtracting the results for Run 2 of the Auramine™ O stain for the results from Run 2 of the dye composition of this invention, and reported in Table 10 below.

TABLE 10

|  | Reticulocyte | IRF |
| --- | --- | --- |
| Mean Difference | +0.50 | +0.08 |
| SD of Difference | 1.40 | 0.143 |

Once determined, these values were compared with the values as noted in the product requirement specification for the LH 750™ hematology system (Beckman Coulter Corp) using the Methylene Blue™ dye. See, Table 11.

TABLE 11

| Parameter Population | Mean Difference | SD of Difference |
| --- | --- | --- |
| % Reticulocyte | ±1.5 | ≦3.00 |

These data demonstrate that the mean difference and SD of difference for the % reticulocytes are similar to the performance specifications of the Beckman Coulter LH 750™ hematology system.

Example 3

This example demonstrates the effect of the compositions of the present invention to analyze whole blood for reticulocyte content. Specifically, compositions with and without blocking agents were prepared and analyzed for reticulocyte content.

One composition of the present invention was prepared by combining 2 μl of a 1 mM solution of the Acridine Orange dye and 1 ml of the sphering agent maltoside in 2 μl of whole blood to form a mixture, the mixture incubated for about 1–5 minutes at room temperature and the mixture analyzed for reticulocyte content.

A second composition of the present invention was prepared by combining 10 μl of a 20 mM solution of the Hoechst™ 33258 blocking agent, 2 μl of a 1 mM solution of the Acridine Orange dye, and 1 ml of the sphering agent maltoside in 2 μl of whole blood to form a mixture, the mixture incubated for about 1–5 minutes at room temperature and the mixture analyzed for reticulocyte content.

The results are illustrated in the cytograms of FIGS. 1A–1D. These data illustrate that when a blocking agent is utilized in combination with the Acridine Orange dye and sphering agent, both the kinetics and non-specific staining of the red cell population is decreased, thereby enhancing the separation of the fluorescent positive population of reticulocytes. Specifically, it is noted that without the blocking agent and when kinetics are occurring, the first interval shows 0.62% reticulocytes and the second half of the interval shows 2.96% reticulocytes with a average over the interval of 2.1% reticulocytes. See FIGS. 1A and 1B.

The addition of the blocking agent over the same time intervals illustrates that the percentage of positive reticulocytes is similar over the interval of segments of the interval. See FIGS. 1C and 1D. By using a composition of the present invention, the binding kinetics are driven by the blocking agent and non-specific binding of the primary dye is minimized.

Example 4

This example discusses the effect of a composition of the present invention in binding to a DNA reference material, e.g., washed, permeabilized avian red cells and to such cells treated with RNAse. Specifically, the binding characteristics and emission spectra compositions of the invention were determined.

Samples containing $1.45 \times 10^4$ rooster whole blood cells/μL in phosphate buffered saline (PBS) (DNA sample) were prepared as stock solutions. Ten percent of the rooster whole blood cells stock solution in 1 mL of diluent was treated with 40 μg/mL of the RNAse stock solution and the solution pre-incubated for 48 hours prior to use in according to the present example.

Stock solutions of compositions of the invention were prepared at the concentrations noted in Table 12. The compositions of the present invention were then prepared by combining a specific amount of each stock solution (see, Table 12) with 1 mL of a diluent selected from the Isoflow™ diluent, n-dodecyl-β-D-maltoside (maltoside—a non-ionic detergent), the flucopyranoside sphering reagent, n-dodecyl-N,N-dimethyl-3-ammonio-1-propane sulfonate (Zwittergent—a pseudo-ionic detergent), or water. These compositions were then separately combined with the samples described above and the fluorescence spectra obtained.

Fluorescence spectra and data were obtained using the RF 5000% Shimadzu™ spectrofluorophotometer having an excitation wavelength (EX) of 488 nanometers (nm), an emission wavelength range (EM range) of 490–800 nm, an EX of 532 nm, an EM of 550–800 nm, a high sensitivity, and a band width of 1.5 at the EX and EM values.

TABLE 12

| Component of Composition | Final Concentration ($\mu$M) of Composition with Diluent | Concentration of Dye Stock Solution (mM) | Amount of Dye Stock Solution ($\mu$L) |
|---|---|---|---|
| Acridine Orange (AO) | 2 | 1 | 2 |
| Thiazole Orange ™ (TO) | 2 | 1 | 2 |
| Pyronin ™ Y (PY) | 2 | 1 | 2 |
| Auramine ™ O (AurO) | 2 | 1 | 2 |
| LDS 752* | 2 | 1 | 2 |
| Hoechst ™ (HO) 33258 | 200 | 20 | 10 |
| Hoechst ™ (HO) 33342 | 200 | 10 | 20 |
| DAPI | 200 | 20 | 10 |

A. Acridine Orange and Acridine Orange/Hoechst™ 33258 Compositions

Data were obtained for the eight samples having the dyes, diluents, and DNA samples as noted in Table 13. Maltoside also serves as a sphering reagent.

TABLE 13

| Sample | Compositions | Diluent | RNAse-treated Cells |
|---|---|---|---|
| A | AO | Maltoside | Yes |
| B | AO | Water | Yes |
| C | AO + HO 33258 | Maltoside | Yes |
| D | AO + HO 33258 | Water | Yes |
| E | AO | Maltoside | No |
| F | AO | Water | No |
| G | AO + HO 33258 | Maltoside | No |
| H | AO + HO 33258 | Water | No |

The fluorescence spectra of samples A–H, with and without RNAse treated cells, were obtained. A single peak at 526 nm was observed for each sample and the fluorescence intensity decreased over time. For samples A–D that contained RNAse treated cells, decreases in fluorescence intensity were observed. Specifically, for samples A–B, which did not contain the blocking agent, a 8.6% intensity decrease over time was noted for sample A and a 6.3% decrease was noted for sample B. For samples C and D, which contained a blocking agent, a marked decrease in fluorescence intensity was noted (about 10 times lower for sample C and about 5 times lower for sample D) as compared to samples A and B. The fluorescence intensity also decreased over time for samples C–D (about 8.6% decrease for sample A, 6.3 decrease for sample B, 52% decrease for sample C and about 51% decrease for sample D). The results in samples C and D indicate that the RNA was preferentially stained by the composition of the present invention.

For cells containing DNA that lacked RNAse, autofluorescence for samples G–H, which contained the blocking agent, decreased (about 10 times lower for sample G and about 2.4 times lower for sample H), thereby illustrating a decrease in fluorescence intensity. It was further noted that the autofluorescence of samples F–H did not change over time, but the autofluorescence of samples E and H decreased over time by about 3.8%.

B. Thiazole™ Orange and Thiazole™ Orange/Hoechst™ 33258 Compositions

Data were obtained for eight samples having the dyes, diluents, and cells as noted in Table 14.

TABLE 14

| Sample | Compositions | Diluent | RNAse-treated Cells |
|---|---|---|---|
| I | TO | Maltoside | Yes |
| J | TO | Water | Yes |
| K | TO + HO 33258 | Maltoside | Yes |
| L | TO + HO 33258 | Water | Yes |
| M | TO | Maltoside | No |
| N | TO | Water | No |
| O | TO + HO 33258 | Maltoside | No |
| P | TO + HO 33258 | Water | No |

The fluorescence spectra of samples I–L, with and without RNAse treated cells, were obtained. A single peak at 526 nm and a variation in fluorescence intensity was observed for each sample. For samples I–J, fluorescence intensity increased after the first minute and thereafter remained constant. However, the fluorescence intensity for samples K–L illustrated a marked decrease in fluorescence intensity (approximately ten times lower for sample K and approximately seven times lower for sample L) when compared to samples I–J. Further, the fluorescence intensity of samples K–L was noted to decrease over time (a 34.5% decrease for sample K and a 12.1% decrease for sample L). The results in samples K and L indicate that the RNA was preferentially stained by the composition of the present invention.

Samples M–P, which did not contain RNAse treated cells, did not exhibit autofluorescence.

C. Pyronin™ Y and Pyronin™ Y/Hoechst™ 33258 Compositions

Data were obtained for eight samples having the dyes, diluents, and DNA cells noted in Table 15.

TABLE 15

| Sample | Compositions | Diluent | RNAse-treated Cells |
|---|---|---|---|
| Q | PY | Maltoside | Yes |
| R | PY | Water | Yes |
| S | PY + HO 33258 | Maltoside | Yes |
| T | PY + HO 33258 | Water | Yes |
| U | PY | Maltoside | No |
| V | PY | Water | No |
| W | PY + HO 33258 | Maltoside | No |
| X | PY + HO 33258 | Water | No |

The fluorescence spectra of samples Q–X were obtained. A single peak at 563.2 nm was observed for each sample, with a decrease in fluorescence intensity over time. For samples Q–T that contained RNAse treated cells, a marked decrease in fluorescence intensity was observed for samples S–T (about 10 times lower for sample S and about 5 times lower for sample T), as compared to samples Q–R. The results in samples S and T indicate that the RNA was preferentially stained by the composition of the present invention. For samples U–X that did not contain RNAse treated cells, the autofluorescence for sample U–V was the same. However, for samples W–X, the autofluorescence was lower (about 10 times lower for sample W and about 2 times lower for sample X), which showed a decrease in fluorescence intensity.

D. LDS 751 and LDS 751/Hoechst™ 33258 Compositions

Data were obtained for eight samples having the dyes, diluents, and DNA cells noted in Table 16.

TABLE 16

| Sample | Compositions | Diluent | RNAse-treated Cells |
| --- | --- | --- | --- |
| AA | LDS | Maltoside | Yes |
| AB | LDS | Water | Yes |
| AC | LDS + HO 33258 | Maltoside | Yes |
| AD | LDS + HO 33258 | Water | Yes |
| AE | LDS | Maltoside | No |
| AF | LDS | Water | No |
| AG | LDS + HO 33258 | Maltoside | No |
| AH | LDS + HO 33258 | Water | No |

The fluorescence spectra of samples AA–AH, with and without RNAse treated DNA cells, were obtained. A single peak at 710.4 nm was observed. The fluorescence intensity for sample AA was very low, i.e., about 1.3 and for sample AD was about 3 times lower than the fluorescence intensity for sample AC. Autofluorescence was not observed for samples AE–AH.

E. Concentration Studies

This example discusses the ability of a composition of the present invention at a range of concentrations to dye cells of sample. Specifically, the effect of dyes binding to RNAse treated DNA-containing cells was assessed to determine binding characteristics and emission spectra of the dyes.

Stock solutions of the HO 33258 blocking agent were prepared at concentrations of 50 $\mu$M, 100 $\mu$M, 200 $\mu$M, 400 $\mu$M, and 800 $\mu$M. Similarly, stock solutions were prepared which contained a dye selected from AO, TO, or PY at concentrations of 0.5 $\mu$M, 1 $\mu$M, 2 $\mu$M, 4 $\mu$M, and 8 $\mu$M. Compositions were thereby prepared by combining each dye solution with each blocking agent stock solution, in a 1:100 ratio, respectively. To this composition was added 1 $\mu$l of the maltoside sphering reagent.

The data (not shown) illustrated that for the AO:HO composition, the optimum concentration is about 2 $\mu$M:200 $\mu$M to about 4 $\mu$M:400 $\mu$M. The 8 $\mu$M:800 $\mu$M solution became cloudy and the emission wavelength increased from about 526.4 to about 528.0. For the solutions that did not contain HO 33258, i.e., where AO was utilized alone, there was no increase in emission wavelength.

For the TO:HO composition, the 8 $\mu$M:800 $\mu$M solution became cloudy and displayed an increase in emission wavelength from about 526.4 nm to 528.0 nm. For the solutions that did not contain HO 33258, i.e., where TO was utilized alone, there was no increase in emission wavelength.

For the PY:HO composition, the optimum working range was about 2 $\mu$M:200 $\mu$M to about 4 $\mu$M:400 $\mu$M and the equilibrium was maintained. The 8 $\mu$M:800 $\mu$M solution became cloudy and the emission wavelength increased from about 563.2 to about 564.8. For the solutions that did not contain HO 33258, i.e., where PY was utilized alone, there was no increase in emission wavelength.

F. Hoechst Equivalence Studies

This example discusses the comparison of the HO 33258 blocking agent with other blocking agents in compositions of the present invention. Specifically, blocking agents including DAPI and HO 33342 were utilized.

(i) The DAPI Blocking Agent

Compositions were prepared by combining the DAPI stock solution, the dye stock solution containing AO, TO, or PY, and either the maltoside sphering reagent or water. These samples were then added to avian ROG cells, with and without treatment with RNAse, and the effect of binding of the composition was assessed to determine binding characteristics of the same.

The data (not shown) illustrated that when DNA-containing cells, without and without treatment with RNAse, were treated with compositions containing AO, DAPI, and the maltoside sphering agent or water, no trend in the emission wavelength or fluorescence intensity over time was noted. However, emission wavelengths were higher for RNAse treated DNA cells (528 nm for solutions containing the maltoside sphering agent and 529.6 nm for solutions containing water). These data therefore illustrate that the fluorescence intensity dampened upon the addition of DAPI, but did not dampen as much as when HO 33258 was utilized.

These data also illustrate that when RNAse treated DNA cells were mixed with compositions containing TO, DAPI, and the sphering agent, the emission wavelength increased and the fluorescent intensity did not display a trend over time. However, when similar cells were treated with compositions containing TO, DAPI, and water, the emission wavelength showed no trend and the fluorescent intensity increased over time.

These data further illustrate that when RNAse treated DNA-containing avian cells were mixed with PY, DAPI, and sphering agent or $H_2O$, no trend in the emission wavelength or fluorescent intensity was observed over time. Fluorescent intensity dampened upon the addition of DAPI, but did not dampen as much as when HO 33258 was utilized, and was lower than the autofluorescence of these compositions.

(ii) The Hoechst™ 33342 Blocking Agent

Compositions were prepared by combining the HO 33342 stock solution, the dye stock solution containing AO or PY, and either the maltoside sphering reagent or water. These samples were then added to ROG cells, with and without treatment with RNAse, and the effect of the composition binding to the cells was assessed to determine binding characteristics.

These data (not shown) illustrated that when RNAse treated DNA cells were treated with AO, HO 33342, and sphering agent or water, a slight decrease in the fluorescent intensity was observed. It was also noted that after subtracting the autofluorescence of the dyes, the fluorescent intensity of the HO 33342 blocking agent and the HO 33258 blocking agent were similar. These data also illustrate that when RNAse treated DNA cells were mixed with AO, HO 33342, and sphering agent or water, no trend in emission wavelength or fluorescence intensity was observed over time.

The data further illustrated that when RNAse treated DNA reference avian red cells were mixed with PY, HO 33342, and sphering agent or $H_2O$, no trend in the emission wavelength was noted over time, but the fluorescent intensity dampened upon the addition of HO 33342. Further, for the unaltered DNA-containing avian cells, no trend in emission wavelength or fluorescence was observed over time and the autofluorescence of PY and the PY/HO 33342 compositions were higher than fluorescent intensity of these dyes when unbound to ROG cells.

G. Specificity Studies

This example discusses the specificity of compositions of the invention containing the HO 33258 blocking agent using DNA reference avian red cells and RNAse treated cells.

Compositions containing the HO 33258 blocking agent, the maltoside sphering agent, and a dye selected from AO, TO, and PY were prepared as described above. These samples were then added to DNA reference avian cells, with and without treatment with RNAse, and the effect of the composition binding to the cells was assessed to determine binding characteristics.

The data illustrate that when using the AO and TO compositions, there was no effect on the fluorescent intensity upon the addition of RNAse to the treated cells. However, when using the composition containing the PY dye, a higher fluorescence intensity was noted.

H. Sphering Reagent Permeabilization Study

This example evaluates the effect of the compositions of the invention with different sphering reagents including maltoside, n-dodecyl-β-D-glucopyranoside (Glucopyranoside—a non-ionic detergent) and Zwittergent 3–12 to bind to DNA reference material, the ROG cells, both with and without treatment with RNAse.

Compositions containing HO 33258, a dye selected from AO or PY, and sphering agent were prepared as described above. These samples were then added to DNA reference cells, with and without treatment with RNAse, and the effect of the composition binding to the cells was assessed to determine binding characteristics.

These data (not shown) illustrated that compositions each having a different sphering agent all produced peaks of similar intensities, regardless of the dye utilized in the composition and DNA cells tested.

Example 5

This example discusses the effect of a composition of the present invention in binding to DNA reference cells and RNAse treated cells at varying ratios. Specifically, the binding characteristics and emission spectra of a composition of the invention were determined.

Compositions of the present invention were prepared by combining a red dye including the TO-PRO-3™ Iodide dye, the R1 dye and the R2 dye with a blocking agent including the Orcein™ dye, the Pentoxifilline™ dye, bis-Benzimide, the Phloxine™ dye, or the Quinacrine™ dye, in the Isoflow™ A38 diluent as noted in Table 17. Each mixture noted in Table 17 was then added to a sample containing RNA, and the mixture incubated for 1–5 minutes at room temperature, and the fluorescence spectra obtained. Table 17 provides the formulation of the compositions and % reticulocytes detected in the samples. Fluorescence spectra and data were obtained using conventional apparatus.

TABLE 17

| Dye | Blocking Agent | Molar Ratio of Blocking Agent:Dye | | | | Fold Reduction of Non-Specific Staining (%) | | |
|---|---|---|---|---|---|---|---|---|
| | | 0:1 | 50:1 | 100:1 | 150:1 | 50 | 100 | 150 |
| TO-PRO | Orcein | 84.67 | 84.67 | 67.26 | | 0 | 21 | |
| R1 | Orcein | 143.04 | 114.36 | 101.5 | | 20 | 29 | |
| R2 | Orcein | 90.81 | 82.62 | 77.50 | | 9 | 15 | |
| R1 | Pentoxifilline | 143.04 | 143.04 | 113.34 | 89.79 | 0 | 21 | 37 |
| R2 | Pentoxifilline | 90.81 | | 88.76 | 80.57 | | 2 | 11 |
| R1 | bis-Benzimide | 143.04 | | 116.41 | 106.17 | | 19 | 26 |
| R2 | bis-Benzimide | 90.81 | | 90.81 | 91.84 | | 0 | -1 |
| R1 | Phloxine B | 143.04 | | 79.55 | 62.14 | | 44 | 57 |
| R2 | Phloxine B | 90.81 | | 62.14 | 48.83 | | 32 | 46 |
| R1 | Quinacrine | 143.04 | | 95.93 | 83.64 | | 33 | 42 |
| R2 | Quinacrine | 90.81 | | 74.43 | 68.28 | | 18 | 25 |

These data illustrate that the non-specific staining of the red blood cells is reduced by about 57% by the addition of the Phloxine™ dye in combination with the R1 red dye at a 150-fold excess.

All documents cited above are incorporated by reference herein. The compositions and processes of the present invention are believed to be encompassed by the scope of the claims appended hereto.

What is claimed is:

1. A composition for enhancing differential staining of RNA, DNA and granules in a sample comprising cells, said composition comprising:
    a first fluorescent dye that can bind specific binding sites and non-specific binding sites in said sample, said first dye emitting fluorescence at a first wavelength; and
    a second non-intercalating dye that competes with said first dye for binding to said nonspecific binding sites, said second dye emitting fluorescence at a second wavelength different from said first wavelength, wherein the molar ratio of said second dye and said first dye is at least about 20:1.

2. A composition for enhancing differential staining of RNA, DNA and granules in a sample comprising cells, said composition comprising:
    a first fluorescent metachromatic dye that can bind specific binding sites and non-specific binding sites in said sample, said first dye emitting fluorescence at a first wavelength; and
    a second non-intercalating dye that competes with said first dye for binding to said nonspecific binding sites, said second dye emitting fluorescence at a second wavelength different from said first wavelength, wherein the molar ratio of said second dye and said first dye is at least about 20:1.

3. The composition according to claim 2, wherein said metachromatic dye is a dye selected from the group consisting of Acridine Orange dye, nonyl Acridine Orange dye, Acridine Red dye, Toluidine Blue dye, SYTO™ dye, TOTO™ dye, YOYO™ dye, and BOBO™ dye.

4. The composition according to claim 2, wherein said metachromatic dye is cell permeant.

5. The composition according to claim 2, wherein said metachromatic dye is a cell-impermeant dye and wherein said composition further comprises a cell permeabilizing or sphering agent.

6. The composition according to claim 2, wherein said metachromatic dye is an intercalating dye.

7. The composition according to claim 1, wherein said first dye is propidium iodide or Thiazole Orange dye.

8. The composition according to claim 2, wherein said metachromatic dye is a non-intercalating dye.

9. The composition according to claim 1, wherein said first dye is a non-metachromatic dye.

10. The composition according to claim 1, wherein said first dye is a cell permeant dye.

11. The composition according to claim 9, wherein said first dye is a cell-impermeant dye and wherein said composition further comprises a permeabilizing or sphering agent.

12. The composition according to claim 9, wherein said non-metachromatic dye is selected from the group consisting of Neutral Red dye, Basic Orange 21 dye, DiOC dye and combinations thereof.

13. The composition according to claim 1 or 2, wherein said second dye is selected from the group consisting of 2'-(4-hydroxyphenyl)-5-(4-methyl-1-peperazinyl)-2,5-bis- 1 H-benzimidazole trihydrochloride pentahydrate bisbenzimide; Hoechst 34580; 2'-(ethoxyphenyl)-5-(4-methyl-1-peperazinyl)-2,5-bis- 1 H-benzoimdazole trihydrochloride trihydrate bisbenzimide; 4',6-bis-[2-imidazoxolinyl-4H, 5H]-2-phenyl-indole; Pentoxiphilline, Phloxine B, Eosin Y; Quinacrine; Orcein; bis-Benzimide; and combinations thereof.

14. The composition according to claim 1 or 2, wherein the molar ratio of said second dye to said first dye is between about 20:1 to about 500:1.

15. The composition according to claim 14, wherein the molar ratio of said second dye to said first dye is between about 50:1 to about 300:1.

16. The composition according to claim 15, wherein the molar ratio of said second dye to said first dye is about 100:1.

17. The composition according to claim 1, further comprising a third dye.

18. The composition according to claim 1, further comprising a permeabilizing agent or a sphering agent.

19. The composition according to claim 2, further comprising a permeabilizing agent or a sphering agent.

20. The composition according to claim 1 or 2, further comprising a solvent.

21. The composition according to claim 1 or 2, wherein said cells in said sample are mammalian cells.

22. The composition according to claim 21, wherein said cells are selected from the group consisting of red blood cells, white blood cells, reticulocytes, blast cells, nucleated red blood cells, basophils, mast cells, neutrophils, lymphocytes, monocytes, eosinophils, platelets, and combinations thereof.

23. The composition according to claim 2, wherein said first dye is Acridine Orange and said second dye is selected from the group consisting of 2'-(4-hydroxyphenyl)-5-(4-methyl-1-peperazinyl)-2,5 -bis-1 H-benzimidazole trihydrochloride pentahydrate benzimide blocking agent and 2'-(ethoxyphenyl)-5-(4-methyl-1-peperazinyl)-2,5-bis-1 H-benzoimidazole trihydrochloride trihydrate bisbenzimide blocking agent, wherein said molar ratio is about 100:1.

24. The composition according to claim 23, further comprising a permeabilizing agent or a sphering agent.

25. The composition according to claim 2, wherein said first dye is Acridine Orange or TOTO™ dye, and wherein said composition further comprises a permeabilizing agent or a sphering agent.

26. A method for enhancing differential staining of RNA, DNA and granules in a sample comprising cells, said method comprising the steps of:
    (a) contacting said sample with the composition of claim 1 or claim 2, and
    (b) analyzing said sample to detect differential expression of said RNA, DNA and granules in said sample.

27. The method according to claim 26, further comprising the step of permeabilizing said cells to penetration of dyes in said composition before contacting step (a).

28. The method according to claim 26, wherein said cells are selected from the group consisting of reticulocytes, blast cells, and nucleated red blood cells.

29. The method according to claim 26, wherein said cells are selected from the group consisting of red blood cells, white blood cells, reticulocytes, blast cells, nucleated red blood cells, basophils, mast cells, neutrophils, lymphocytes, monocytes, eosinophils, platelets and combinations thereof.

30. A diagnostic kit for enhancing differential staining of RNA, DNA and granules in a sample comprising cells, said kit comprising:
    (a) a first fluorescent metachromatic dye that can bind specific binding sites and non-specific binding sites in said sample, said first dye emitting fluorescence at a first wavelength; and
    (b) a second non-intercalating dye that competes with said first dye for binding to said nonspecific binding sites, said second dye emitting fluorescence at a second wavelength different from said first wavelength, wherein the molar ratio of said second dye and said first dye is at least about 20:1.

31. The kit according to claim 30, further comprising a permeabilizing agent to enhance permeabilization of said dyes into said cells or a sphering agent.

32. The kit according to claim 30, wherein said first dye is the Acridine Orange dye and said second dye is 2'-(ethoxyphenyl)-5-(4-methyl-1 -peperazinyl)-2,5-bis-1 H-benzoimidazole trihydrochloride trihydrate bisbenzimide.

33. The kit according to claim 30, further comprising a buffer.

34. The kit according to claim 30, wherein said cells are platelets.

35. The method according to claim 26, wherein said cells are platelets.

36. A method for analyzing cells and cell maturation in a sample containing cells, said method comprising the steps of:
    (a) contacting said sample with the composition of claim 1 or 2; and
    (b) analyzing said sample to detect differential staining of said cells indicative of the maturation of said cells.

37. The method according to claim 36, wherein said cells are platelets.

38. The method according to claim 36, wherein said cells are red blood cells.

39. A method for detecting the maturation of platelets in a sample comprising platelets, said method comprising the steps of:
    (a) contacting said sample with the composition of claim 1 or 2; and
    (b) analyzing said sample to detect differential staining indicative of the maturation of said platelets.

40. The method according to claim 39, wherein said sample further comprises red blood cells.

* * * * *